(12) United States Patent
Newman et al.

(10) Patent No.: US 7,745,108 B2
(45) Date of Patent: Jun. 29, 2010

(54) METHOD FOR IDENTIFYING TERPENE SYNTHASE

(75) Inventors: Jack D. Newman, Berkeley, CA (US); Neil Renninger, Albany, CA (US); Vincent J. J. Martin, Kensington, CA (US); Jay D. Keasling, Berkeley, CA (US); Keith Kinkead Reiling, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 661 days.

(21) Appl. No.: 10/581,975

(22) PCT Filed: Dec. 8, 2004

(86) PCT No.: PCT/US2004/041876

§ 371 (c)(1),
(2), (4) Date: May 23, 2007

(87) PCT Pub. No.: WO2005/057176

PCT Pub. Date: Jun. 23, 2005

(65) Prior Publication Data

US 2007/0264632 A1    Nov. 15, 2007

Related U.S. Application Data

(60) Provisional application No. 60/528,373, filed on Dec. 9, 2003.

(51) Int. Cl.
*C12Q 1/00* (2006.01)

(52) U.S. Cl. ............................ 435/4; 435/468; 536/23.2

(58) Field of Classification Search ..................... 435/4, 435/468; 536/23.2
See application file for complete search history.

(56) References Cited

U.S. PATENT DOCUMENTS 5,571,681 A * 11/1996 Janda ........................... 506/10
2003/0148479 A1* 8/2003 Keasling et al. ............. 435/131

OTHER PUBLICATIONS

Cane D. et al. Trichodiene Synthase: Mechanism Based Inhibition of a Sesquiterpene Cyclase. Bioorganic & Medicinal Chemistry Letters 9:1127-1132, 1999.*

Croteau R. et al. Irreversible Inactivation of Monoterpene Cyclases by a Mechanism Based Inhibitor. Archives of Biochemistry and Biophysics 307(2)397-404, Dec. 1993.*

(Continued)

*Primary Examiner*—Ralph Gitomer
(74) *Attorney, Agent, or Firm*—Paula A. Borden; Bozicevic, Field & Francis LLP

(57) ABSTRACT

The present invention provides a method of identifying an enzyme, the method generally involving contacting a sample containing an enzyme with a selected enzyme substrate, where the contacting provides for covalent binding of the substrate to an amino acid of the enzyme to form a covalently modified enzyme; and determining the amino acid sequence of at least a portion of the covalently modified enzyme, using any available peptide sequencing technology, such as tandem mass spectrometry. The present invention further provides methods of identifying a nucleic acid encoding an enzyme, the methods generally involving identifying an enzyme; and, based on the amino acid sequence of at least a portion of the enzyme, designing nucleic acid probes or primers that hybridize to the nucleic acid encoding the enzyme.

19 Claims, 5 Drawing Sheets

OTHER PUBLICATIONS

Garcia-Allen L. et al. Mechanism Based Inhibition of Enzyme I of the *E. coli* Phosphotransferase System. J of Biological Chemistry 277(9)6934-42, Mar. 1, 2002.*

Britton et al. (2001) Synthetic Transformations of Eleutherobin Reveal New Features of Its Microtubule-Stabilizing Pharmacophore, *J Am Chem Soc* 123(35):8632-8633.

Chang et al. (2002) The barbamide biosynthetic gene cluster: a novel marine cyanobacterial system of mixed polyketide synthase (PKS)-non-ribosomal peptide synthetase (NRPS) origin involving an unusual trichloroleucyl starter unit, *Gene* 296(1-2):235-247.

Chen et al. (1999) The Total Synthesis of Eleutherobin, *J Am Chem Soc* 121:6563-6579.

Davidson et al. (2001) Evidence for the Biosynthesis of Bryostatins by the Bacterial Symbiont *Candidatus* Endobugula sertula of the Bryozoan *Bugula neritina*, *Appied Environmental Microbiology*, 67(10):4531-4537.

Figeys et al. (1996) Protein identification by capillary zone electrophoresis/microelectrospray ionization-tandem mass spectrometry at the subfemtomole level., *Anal. Chem.* 68:1822-1828.

Hamel et al.(1999) The Coral-Derived Natural Products Eleutherobin and Sarcodictyins A and B: Effects on the Assembly of Purified Tubulin with and without Mirobubule-Associated Proteins and Binding at the Polymer Taxoid Site, *Biochemistry* 38(17):5490-5498.

Hunt et al. (1986) Protein Sequencing by Tandem Mass Spectrometry, *Proc. Natl. Acad. Sci. USA* 83:6233-6237.

Johnson et al. (1988) Collision-Induced Fragmentation of (M+H) + Ions of Peptides. Side Chain Specific Sequence Ions, *International Journal of Mass Spectrometry and Ion Processes, Mass Spectrometry and Ion Processes* 86:137-154.

Martin et al. (2003) Engineering a mevalonate pathway in *Escherichia coli* for production of terpenoids, *Nature Biotechnology* 21(7):796-801.

Nicolaou et al. (1999) Total Synthesis and Chemical Biology of the Sarcodictyins, *Chem Pharm Bull (Tokyo)* 47(9):1199-1213.

Papayannopoulos (1995) The Interpretation of Collision-Induced Dissociation Tandem Mass Spectra of Peptides, *Mass Spectrometry Reviews* 14:49-73.

Shevchenko et al. (1996) Linking genome and proteome by mass spectrometry: Large scale identification of yeast proteins from two dimensional gels, *Proc. Natl. Acad. Sci. U.S.A.* 93:14440-14445.

Wang et al. (1999) Engineered Isoprenoid Pathway Enhances Astaxanthin Production in *Escherichia coli Biotechnology and Bioengineering* 62(2):235-241.

Wilm et al. (1996) Femtomole sequencing of proteins from polyacrylamide gels by nano-electrospray mass spectrometry, *Nature* 379:466-469.

* cited by examiner

METHOD FOR IDENTIFYING TERPENE SYNTHASE

CROSS-REFERENCE

This application claims the benefit of U.S. Provisional Patent Application No. 60/528,373 filed Dec. 9, 2003, which application is incorporated herein by reference in its entirety.

FIELD OF THE INVENTION

This invention relates to a method for identification of enzymes from diverse organisms.

BACKGROUND OF THE INVENTION

A majority of the drugs and fine chemicals in use today are natural products or their derivatives. The source organisms (e.g., trees, marine invertebrates) of many of these natural products are neither amenable to the large-scale cultivation necessary to produce commercially viable quantities nor to genetic manipulation for increased production or derivatization of these compounds. Therefore, the natural products must be produced semi-synthetically from analogs or synthetically using conventional chemical syntheses. Furthermore, many natural products have complex structures, and, as a result, are currently uneconomical or impossible to synthesize. Such natural products must be either extracted from their native sources, such as trees, sponges, corals and marine microbes; or produced synthetically or semi-synthetically from more abundant precursors. Extraction of a natural product from a native source is limited by the availability of the native source; and synthetic or semi-synthetic production of natural products suffers from low yield. Such low yields and limited availability of the natural source can restrict the commercial and clinical use of such products. The biosynthesis of natural products in microbes could tap the unrealized commercial and therapeutic potential of these natural resources and yield less expensive and more widely available fine chemicals and pharmaceuticals. In many instances, however, the enzymes involved in production of clinically or industrially important compounds in a living organism are unknown.

Terpenes are examples of such natural products that are structurally complex and difficult or impossible to synthesize with currently available methods. Terpenes have enormous commercial, scientific, and public health potential. The development of therapeutic terpenes is of particular interest for cancer treatment. Examples of known or potential pharmaceutically important terpenes are taxol, artemisin, eleutherobin, and the sarcodictyins.

Taxol and its derivative Taxotere are two powerful anticancer diterpenes used to battle not only breast and lung cancers but also Kaposi's sarcoma. The success of the diterpene Taxol, which was isolated from the bark of the pacific yew tree, has validated the importance of terpene natural products as chemotherapeutics. Eleutherobin and sarcodictyins are potential anti-cancer compounds that share a eunicellane backbone structure and exhibit Taxoid-like modes of action. Eleutherobin was first isolated in 1995 from a soft coral (*Eleutherobia* sp. *Alcyonacea Alcyoniidae*), while the sarcodictyins were first isolated in 1987 from the Mediterranean stoloniferan coral *Sarcodictyon roseum*.

Despite the development of total chemical syntheses, supply limitations still hamper efforts to bring eleutherobin and the sarcodictyins to the clinic. Currently available synthetic routes for production of eleutherobin and the sarcodictyins are far too costly to satisfy the needs of clinical trials and to meet downstream demand. However, these synthesis studies have demonstrated that eleutherobin and its precursors can be used as starting materials for the chemical synthesis of derivatives. Economical production of eleutherobin and the sarcodictyins or of a common structural component for use as a chemical synthon is needed to further develop these promising anticancer compounds. As an alternate source of supply, eleutherobin can be isolated from the aquarium coral *Erythropodium caribaeorum*; however, based upon the large amounts that would be required each year to meet market demand, the slow growth rates of soft coral make harvesting eleutherobin from its natural source impractical.

Every year numerous terpene-derived compounds with promising therapeutic properties are discovered and isolated from corals, sponges, microbes, and plants. The commercial development of these molecules can be limited by the trace quantities present in the natural sources. Therefore, there is a continuing need to develop methods of expressing the terpene biosynthetic genes in microbes, to enable scarce terpenes to be produced in the quantities required for clinical use. In spite of the progress in this field, most commercially relevant terpene synthases have not been cloned and the number of cloned terpene synthases falls far short of the number of identified terpenoid compounds. In addition, the lack of sequence identity among terpene synthases from different organisms and the low-throughput nature of current cloning methods preclude rapid screening, identification and expression of these genes. Furthermore, existing gene discovery methods are time and labor intensive and not amenable to the high-throughput cloning of terpene synthases or the generation of large gene libraries for combinatorial biosynthesis.

Current methods for identification of previously uncharacterized enzymes include (1) use of DNA encoding a known enzyme to identify genes with a similar nucleic acid sequence; (2) use of partial protein sequences from a known, purified enzyme to design degenerate probes for screening libraries; and (3) use of a similarity-based polymerase chain reaction (PCR) where highly conserved regions of the enzyme are used to design degenerate PCR primers and amplify a region of a nucleic acid that encodes an enzyme related to the known enzyme. Such methods rely on some subset of the following criteria: the ability to target conserved sequences with a nucleic acid probe or oligonucleotides, the ability to generate enriched cDNA libraries, the ability to purify the enzyme from tissue, or the ability to express a functional enzyme in a library host. Thus, there is a need in the art for additional methods for identifying new enzymes, where the methods avoid, or are at least less hampered by, such limitations.

The present invention addresses this need by providing a method for identification of new enzymes.

LITERATURE

Davidson et al. (2001) *Appl Environ Microbiol* 67(10): 4531-7; Chang et al. (2002) *Gene* 296(1-2):235; Wang et al. (1999) *Biotechnol Bioeng* 62(2):235-41; Martin et al. (2003) *Nature Biotechnology* 21(7):796-801; Hamel et al. (1999) *Biochemistry* 38(17):5490-8; Chen et al. (1999) *J Am Chem Soc* 121:6563; Nicolaou et al. (1999) *Chem Pharm Bull (Tokyo)* 47(9):1199-213; Britton et al. (2001) *J Am Chem Soc* 123(35):8632-3; Hunt et al. (1986) *Proc. Natl. Acad. Sci. USA* 83:6233-6237; Johnson et al. (1988) *Int. J Mass Spectrom. Ion Processes* 86:137-154; Papayannopoulos (1995) *Mass Spectrom. Rev.* 14:49-73; Shevchenko et al. (1996) *Proc. Natl. Acad Sci. U.S.A.* 93:14440-14445; Figeys et al. (1996)

*Anal. Chem.* 68:1822-1828; and Wilm et al. (1996) *Nature* 379:466-469; U.S. Pat. No. 5,571,681.

SUMMARY OF THE INVENTION

The present invention provides a method of identifying an enzyme, the method generally involving contacting a sample containing an enzyme with a selected enzyme substrate, where the contacting provides for covalent binding of the substrate to an amino acid of the enzyme to form a covalently modified enzyme; and determining the amino acid sequence of at least a portion of the covalently modified enzyme, using any available peptide sequencing technology, such as tandem mass spectrometry. The present invention further provides methods of identifying a nucleic acid encoding an enzyme, the methods generally involving identifying an enzyme; and, based on the amino acid sequence of at least a portion of the enzyme, designing nucleic acid probes or primers that hybridize to the nucleic acid encoding the enzyme.

DEFINITIONS

Figure 1:
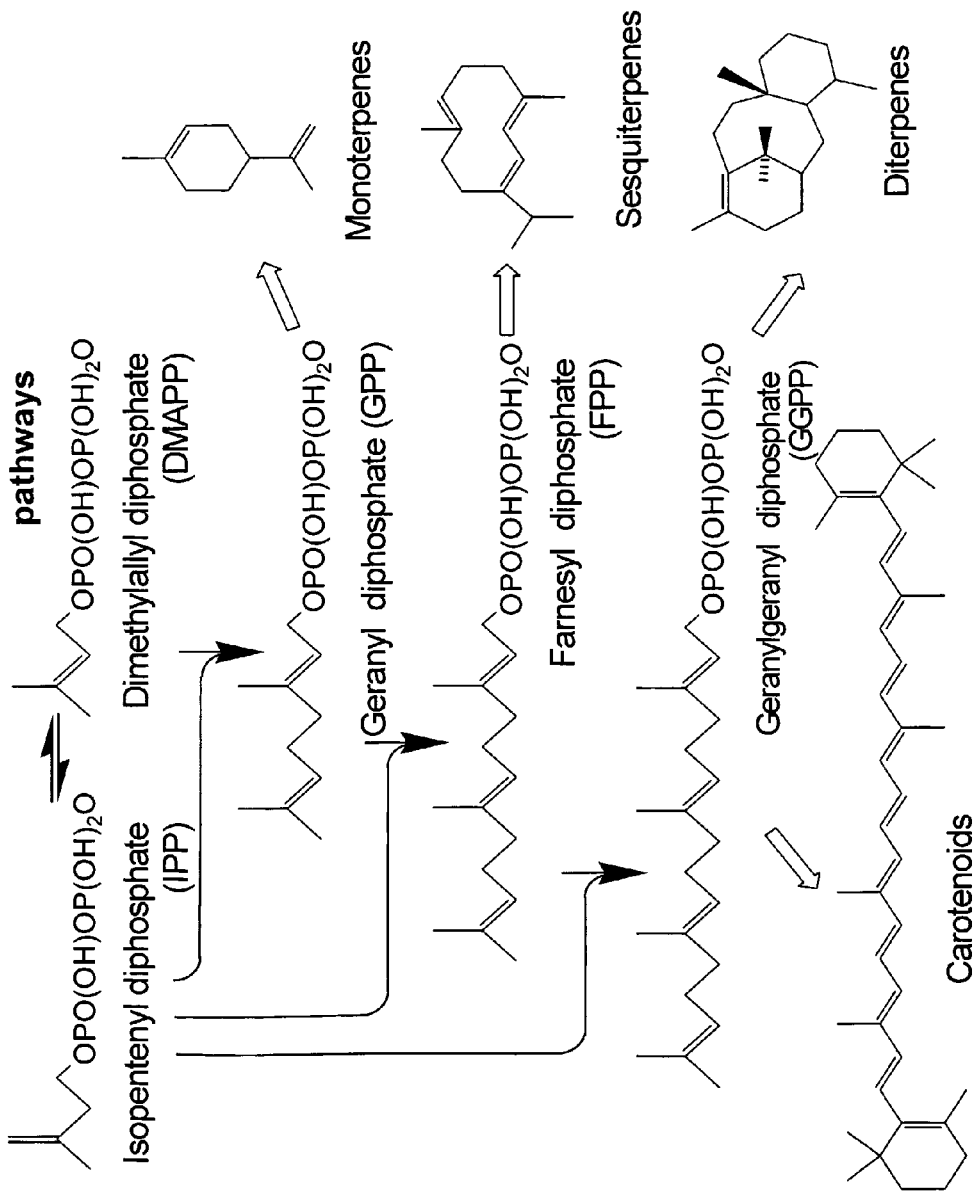
FIG. 1 is a schematic representation of isoprenoid metabolic pathways that result in the production of the terpene biosynthetic pathway intermediates polyprenyl diphosphates geranyl diphosphate (GPP), farnesyl diphosphate (FPP), and geranylgeranyl diphosphate (GGPPP), from isopentenyl diphosphate (IPP) and dimethylallyl diphosphate (DMAPP).

The terms "catalytic polypeptide" and "catalytic moiety" are used interchangeably herein herein to refer to a polypeptide which is capable of changing the rate of a chemical reaction, all other conditions (e.g., temperature, reactant/substrate concentration, etc.) being the same, and which is not, under normal reaction conditions, irreversibly altered by the chemical reaction and, therefore, is not consumed in the reaction. It is also a polypeptide which exhibits the capability of converting multiple moles of reactant/substrate per mole of catalytic antibody; and which, from a mechanistic viewpoint, binds the reactant/substrate, effects the conversion of the reactant/substrate to the product and then releases the product; and which changes the rate of the chemical reaction without shifting the position of the equilibrium. While the aforementioned definitions are characteristics of ideal catalysts, in practice, even the best of catalysts become inhibited or deactivated by contamination in the reaction system or as a result of chemical or physical destruction during the reaction process. For reasons well known in the art, the true operation of a catalyst may be obscured by components of the reaction system or by the condition of the reaction environment. "Normal reaction conditions" expressly exclude reaction conditions that include the presence of a suicide substrate that covalently modifies an amino acid of the enzyme.

The terms "suicide substrate," "mechanism-based inhibitor," "mechanism-based suicide substrate," and "inhibitor analog" are used interchangeably herein to refer to a compound having a structural similarity to a substrate, substrate transition state, or product for a particular enzyme, that, via its normal catalytic mechanism of action, converts the inactivator molecule into a species which without prior release from the active site, binds covalently to that enzyme, thereby inactivating the enzyme. See, e.g., Silverman, R. B. (1988) Mechanism-Based Enzyme Inactivation: Chemistry and Enzymology, Vol. 1 and Vol. 2 (CRC Press, Inc., Boca Raton, Fla.).

A "biological sample" encompasses a variety of sample types obtained from an individual, an environmental sample, an organism, a tissue, a cell, and the like. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations. The term "biological sample" encompasses a clinical sample, and also includes cells in culture, cell supernatants, tissue samples, organs, bone marrow, and the like.

As used herein the term "isolated" is meant to describe a polynucleotide, a polypeptide, or a cell that is in an environment different from that in which the polynucleotide, the polypeptide, or the cell naturally occurs.

The terms "stringent conditions" and "stringent hybridization conditions" are used interchangeably, and refer to conditions under which a probe will hybridize preferentially to its target subsequence, and to a lesser extent to, or not at all to, other sequences. Put another way, the term "stringent hybridization conditions" as used herein refers to conditions that are compatible to produce duplexes between complementary binding members, e.g., between nucleic acid probes and complementary nucleic acids in a sample, e.g., duplexes of nucleic acid probes, such as DNA probes, and their corresponding nucleic acid targets that are present in the sample, e.g., between a DNA probe and its corresponding mRNA present in the sample. The terms "stringent hybridizations" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC (where 1×SSC is 0.15 M NaCl and 15 mM sodium citrate), and 1% sodium dodecyl sulfate (SDS), at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% SDS, 1 mM EDTA at 65° C., and washing in 0.1×SSC/ 0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions that determine whether a nucleic acid is specifically hybridized to a probe. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). Stringent wash conditions for 60-base oligo probes can include washing in 6×SSC/0.005% Triton X-102 for 10 minutes at 25° C. followed by washing in 0.1×SSC/0.005% Triton X-102 for 5 minutes at 25° C. See Sambrook (infra), e.g., for detailed descriptions of equivalent hybridization and wash conditions and for reagents and buffers, e.g., SSC buffers and equivalent reagents and conditions.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

As such, the term "hybridization" refers to the formation of a duplex structure by two single stranded nucleic acids due to complementary base pairing. Hybridization can occur between exactly complementary nucleic acid strands or between nucleic acid strands that contain minor regions of mismatch. As used herein, the term "substantially complementary" refers to sequences that are complementary except for minor regions of mismatch, wherein the total number of mismatched nucleotides is no more than about 3 for a sequence about 15 to about 35 nucleotides in length. Conditions under which only exactly complementary nucleic acid strands will hybridize are referred to as "stringent" or "sequence-specific" hybridization conditions. Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. Computer software for calculating duplex stability is commercially available from a variety of vendors.

Stringent, sequence-specific hybridization conditions, under which an oligonucleotide will hybridize only to the exactly complementary target sequence, are well known in the art (see, e.g., Sambrook et al., 2001, Molecular Cloning—A Laboratory Manual, Cold Spring Harbor Laboratory, Cold Spring Harbor, N.Y.). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridizing conditions allows sequence mismatches to be tolerated; the degree of mismatch tolerated can be controlled by suitable adjustment of the hybridization conditions.

The term "host cell" includes an individual cell or cell culture which can be or has been a recipient of any recombinant vector(s), or isolated nucleic acid, or synthetic nucleic acid, of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a nucleic acid of the invention. A host cell which comprises a recombinant vector of the invention is a "recombinant host cell" or a "genetically modified host cell."

By "transformation" is meant a permanent or transient genetic change induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an enzyme" includes a plurality of such enzymes and reference to "the suicide substrate" includes reference to one or more suicide substrates and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides a method of identifying an enzyme. The method generally involves contacting a sample containing an enzyme with a selected synthetic enzyme substrate, where the contact provides for covalent binding of the substrate to an amino acid in the enzyme, to form a covalently modified enzyme; and determining the amino acid sequence of at least a portion of the covalently modified enzyme. The amino acid sequence is determined using tandem mass spectrometry. The amino acid sequence of at least a portion of the covalently modified enzyme (e.g., a portion of the enzyme surrounding the covalently modified amino acid residue) is in some embodiments used to design degenerate nucleic acid primers, for use in detecting and/or amplifying a nucleic acid that encodes the enzyme.

The present invention is based in part on the observation that new, previously undescribed terpene synthases can be identified by covalently modifying an amino acid in the terpene synthase; and, using a peptide sequencing method such as tandem mass spectrometry, determining the amino acid sequence of at least a portion of the enzyme. Determination of the amino acid sequence is accomplished through use of mass shift signature using mass spectrometry. The entire amino acid sequence can be reconstructed from constituent peptides sequenced by tandem-mass spectrometry or by N-terminal sequencing of the peptides or the native protein. Alternatively, the amino acid sequence can be determined by using the peptide sequence to generate a nucleic acid probe having a degenerate nucleotide sequence, which nucleic acid probe can be used to query a cDNA library or genomic library made from the source of the enzyme; the corresponding cDNA or genomic DNA can be sequenced and translated into the corresponding amino acid sequence.

The present invention is useful for identifying and isolating new enzymes from diverse organisms and environmental samples. A mechanism-based enzyme "tagging" method is first used to covalently modify an enzyme, and tandem mass spectrometry (MS) is then used for the peptide sequencing of the "tagged" protein. The tagging method involves covalently modifying an amino acid in the enzyme with an irreversible inhibitor of the enzyme, also known as a "suicide substrate," forming a covalently modified enzyme. The covalently modified enzyme is subjected to tandem MS, where the amino acid sequence of at least a portion of the enzyme is determined.

The present methods do not rely upon amino acid or nucleotide sequence identity with known enzymes. Instead, the present methods make use of similarities in active site structure or functionality.

A subject method involves contacting a test sample, comprising an enzyme, with a synthetic substrate for a known enzyme, where the synthetic substrate is one that covalently modifies an amino acid in the known enzyme. The synthetic substrate (also referred to as a "suicide substrate") covalently modifies an amino acid within the active site, near the active site, or outside of the active site. In a subject method, a test sample comprises an enzyme and a selected suicide substrate that is known to covalently modify an amino acid of a particular enzyme or class of enzymes.

In many embodiments, the test reaction will be compared to a positive and/or a negative control reaction. A suitable positive control will include a sample comprising an enzyme that is known to be specifically covalently modified by the selected suicide substrate used in the test reaction. For example, where the suicide substrate is a cyclopropylidene farnesyl diphosphate, a suitable positive control will comprise a cyclopropylidene farnesyl diphosphate and a sesquiterpene synthase. Where the suicide substrate is a cyclopropylidene farnesyl diphosphate, a suitable negative control will comprise a cyclopropylidene farnesyl diphosphate and an enzyme that is not covalently modified by cyclopropylidene farnesyl diphosphate, e.g., a β-lactamase.

Suicide Substrates

A wide variety of suicide substrates targeting a wide variety of enzymes can be used in a subject method. Suicide substrates that covalently modify known classes of enzymes are well known in the art, and any suicide substrate can be used to identify an enzyme having attributes similar to those of a known enzyme covalently modified by the same suicide substrate, as well as to identify enzymes that act through a common mechanism. Thus, covalent modification of a polypeptide by a suicide substrate having a known inhibitory activity against a particular enzyme or class of enzymes indicates that the polypeptide is a member of that family of enzymes. For example, if a enzyme is covalently modified by cyclopropylidene farnesyl diphosphate, then it can be assumed that the enzyme is a terpene synthase.

Enzymes for which exist mechanism-based inhibitors include synthetic enzymes and degradative enzymes. Enzymes for which exist mechanism-based inhibitors include, but are not limited to, synthetases, synthases, glucosidases, ribonucleases, peptidases, enzymes that carry out oxidation/reduction reactions, beta-lactamase, decarboxylases, aminotransferases, lyases, racemases, and hydroxylases. For example, difluoromethyl aryl-beta-D-glucosides are known suicide substrates of β-glucosidases (see, e.g., Halazy et al. (1990) *Biooganic Chem.* 18:330-344); difluoromethyl aryl-ribosides are suicide substrates for ribonuclease; beta-lactams are suicide substrates for bacterial beta-lactamases (see, e.g., Silverman (1988) *Mechanism-Based Enzyme Inactivation: Chemistry and Enzymology*, Vol. 1 and Vol. 2 (CRC Press, Inc. Boca Raton, Fla.); and the terpene synthase suicide substrates discussed below. See also, e.g., U.S. Pat. No. 6,177,270.

Terpene synthases form a highly versatile group of enzymes responsible for the biosynthesis of large families of terpene olefins and alcohols from simple polyprenyl diphosphate precursors. The enzymatic synthesis of mono, sesqui, and diterpenes by a synthase is initiated by ionization of an allylic diphosphate ester. Subsequent rearrangements of the carbocation by electrophilic cyclization, methyl or hydride migration followed by elimination of a proton (for olefin), or quenching by water (for alcohols) yields the terpenes. The ability to protect the carbocation from early cyclization termination and to chaperon the precise folding of the substrate in the synthase active site determines the ultimate structure and stereochemistry of the product(s).

Figure 2:
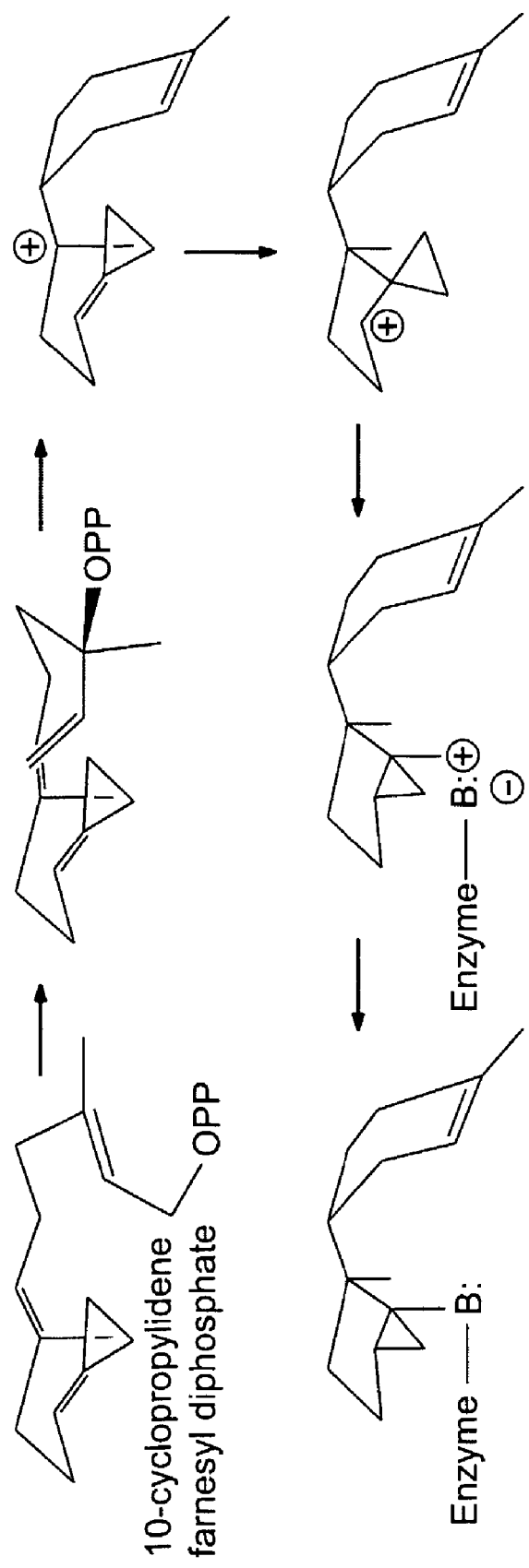
FIG. 2 depicts a hypothetical mechanism for the alkylation of terpene synthases by cyclopropylidene substrate analogs.
Figure 3:
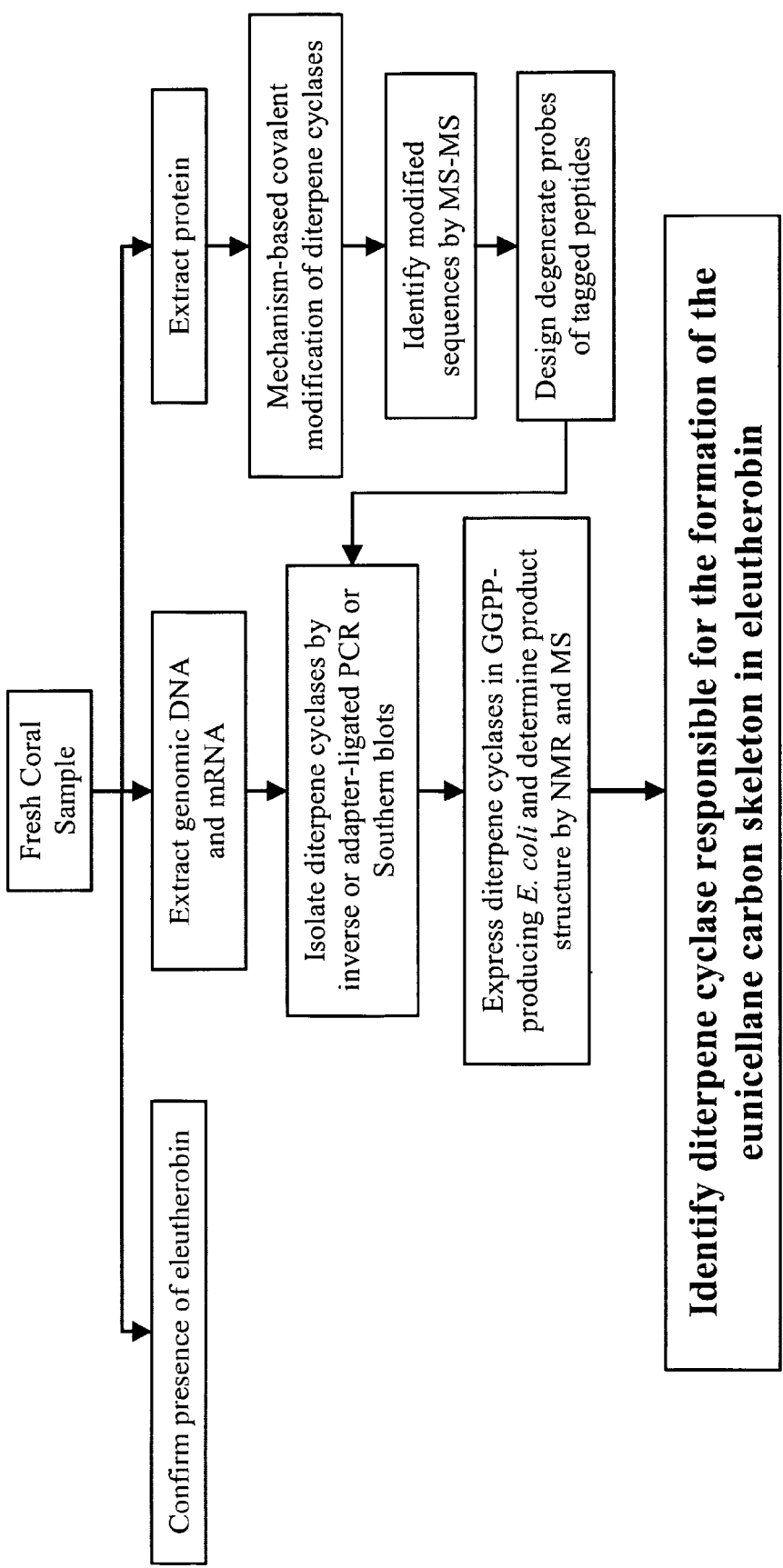
FIG. 3 depicts a flow chart outlining the protocols discussed in Examples 1-4.
Figure 4:
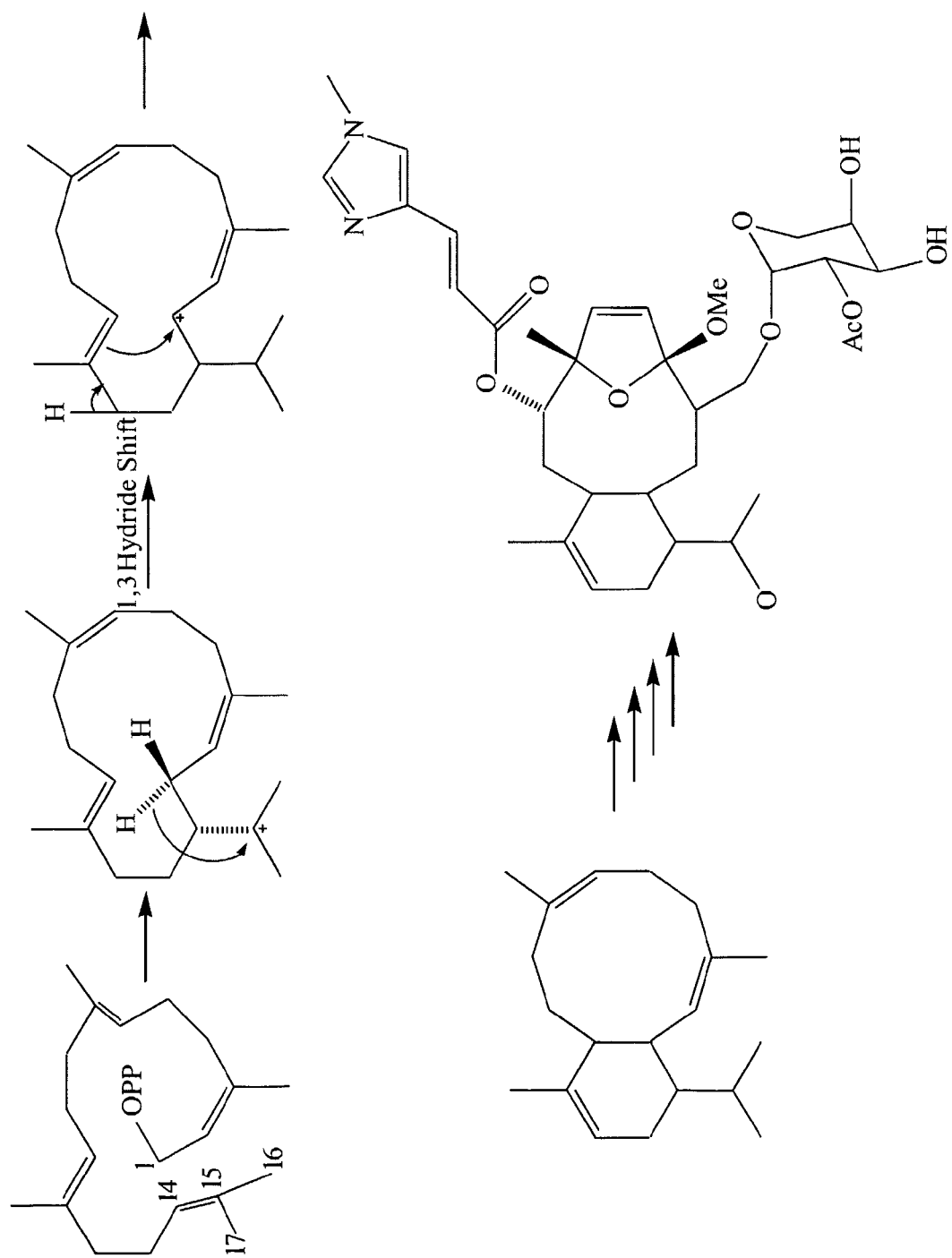
FIG. 4 depicts a proposed mechanism for the cyclization of GGPP to the eunicellane carbon backbone.
Figure 5:
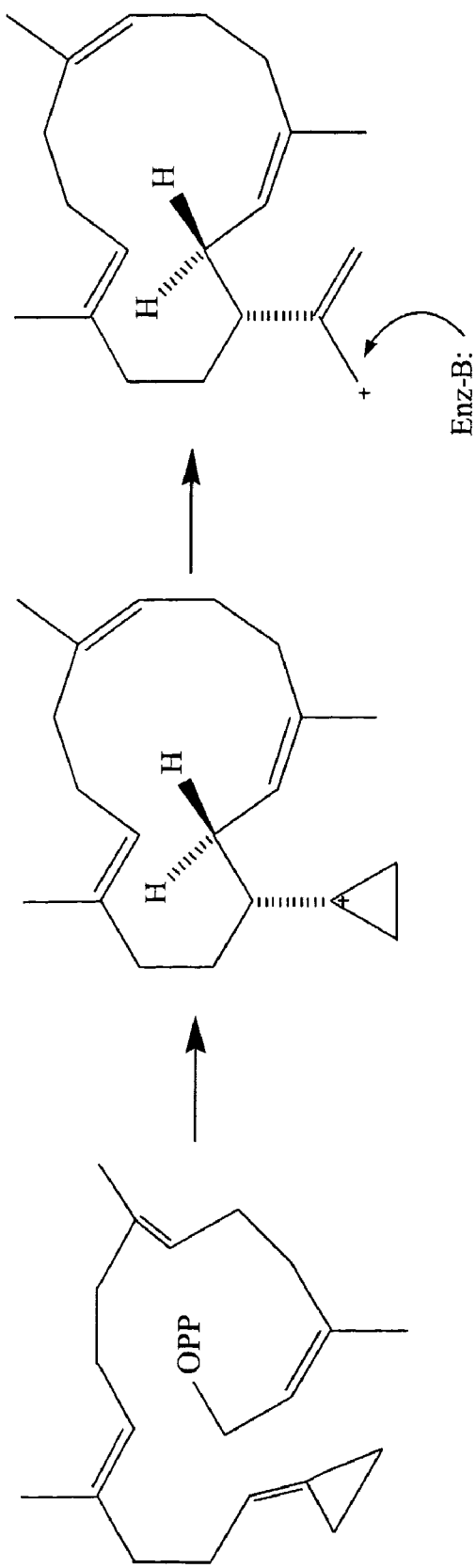
FIG. 5 depicts a proposed mechanism for the covalent modification of the eunicellane diterpene synthase with CP-GGPP.

Mechanism-based suicide substrates have been used in an attempt to identify important terpene synthase catalytic residues (Croteau et al. (1993) Archives of Biochemistry and Biophysics 307(2):397-404; Cane et al. (1999) *Bioorganic & Medicinal Chemistry Letters* 9(8):1127-1132). GPP, FPP, and GGPP substrate analogues containing a cyclopropyl group function as strong mono-, sesqui-, or diterpene synthase inhibitors. The inhibitor enters the active site, and begins cyclization until forming a cyclopropyl or cyclopropylcarbonyl cation (FIG. 2). This intermediate delocalizes and stabilizes the carbocation, which can then react with nearby amino acids containing nucleophilic side chains.

The inhibitor results of Croteau and Cane, supra, demonstrated that cyclopropylidene analogs are substrates to synthases and are capable of alkylating (tagging) the enzymes. All twelve monoterpene synthases tested were sensitive to the cyclopropylidene geranyl diphosphate (CP-GPP) inhibitor, indicating that this mechanism-based method of "tagging" terpene synthases has broad applicability. Efforts were also directed at using the inhibitors to discover synthases from crude protein extracts and to identify the modified residues. In one instance, tagging of limonene synthase by $^3$H-labeled CP-GPP was used to identify the enzyme from a crude protein preparation of spearmint gland extract. Such identification could be performed using gel electrophoresis, liquid chromatography, or other protein separation method.

One could also use radiolabeled inhibitor in one set of tagging experiments to determine the electrophoretic or chromatographic properties of a tagged enzyme. One could subsequently use non-radiolabeled inhibitor in an otherwise identical set of tagging experiments, purifying the non-radiolabeled, tagged enzymes by the above determined electrophoretic or chromatographic properties. For example, in some embodiments, a subject method involves: i) contacting a first test sample comprising a first sample (e.g., a biological sample) comprising an enzyme with a radiolabelled selected suicide substrate, where the contacting provides for covalent binding of the substrate to an amino acid of the enzyme, to form a covalently modified, radiolabelled enzyme; ii) contacting a second test sample comprising a first sample (e.g., a biological sample) comprising an enzyme with the same selected suicide substrate (but not radiolabelled), where the contacting provides for covalent binding of the substrate to an amino acid of the enzyme, to form a covalently modified, non-radiolabelled enzyme; iii) determining the purification properties of the covalently modified, radiolabelled enzyme; and iv) using the purification properties determined in step (iii), purifying the non-radiolabelled enzyme.

"Purification properties" refers to the steps necessary to perform to purify a given enzyme. Purification properties include the fraction (e.g., time and/or volume) in which a given enzyme elutes from a fast protein liquid chromatography column; the position at which a given enzyme migrates in a two-dimensional gel electrophoresis purification scheme; and the like.

Suitable suicide substrates for use in identifying terpene synthases include cyclopropyl-modified polyprenyl diphosphates. Suitable cyclopropyl-modified polyprenyl diphosphates include, but are not limited to, cyclopropylidene farnesyl diphosphate, cyclopropylidene geranyl diphosphate, cyclopropylidene geranylgeranyl diphosphate, cyclopropylidene geranylfarnesyl diphosphate, cyclopropylidene hexaprenyl diphosphate, cyclopropylidene heptaprenyl diphosphate, cyclopropylidene octaprenyl diphosphate, cyclopropylidene solanesyl diphosphate, cyclopropylidene decaprenyl diphosphate, cyclopropylidene undecaprenyl diphosphate, and cyclopropylidene dehydrodolichyl diphosphate. Other suitable suicide substrates for use in identifying terpene synthases include vinyl analogs of polyprenyl diphosphates. Suitable vinyl analogs of polyprenyl diphosphates include, but are not limited to, 6-methylidene farnesyl diphosphate, 11-methylidene geranyl diphosphate, 16-methylidene geranylgeranyl diphosphate, 21-methylidene geranylfarnesyl diphosphate, 26-methylidene hexaprenyl diphosphate, 31-methylidene heptaprenyl diphosphate, 36-methylidene octaprenyl diphosphate, 41-methylidene solanesyl diphosphate, 46-methylidene decaprenyl diphosphate, and 51-methylidene undecaprenyl diphosphate.

In some embodiments, the suicide substrate will be detectably labeled, so as to facilitate identification of the enzyme to which it is covalently bound. Detectable labels include direct labels and indirect labels. Direct labels provide a signal, and include, but are not limited to, radiolabels such as $^3$H, $^{125}$I, $^{131}$I, $^{32}$P, $^{13}$C, and the like; fluorophores; chromophores; luminescent compounds; and the like. Indirect labels include labels that do not themselves provide a signal but that, together with one or more additional moieties provide for a detectable signal. Suitable indirect labels include, but are not limited to, biotin, e.g., for detection with avidin, such as detectably-labeled avidin; haptens, detectable with an antibody or hapten-binding antibody fragment; and the like. Detectable labels for avidin or antibodies include enzymes such as alkaline phosphatase, horse radish peroxidase, luciferase, and the like; fluorogenic and/or chromogenic proteins; a green fluorescent protein (GFP) derived from *Aequoria victoria* or a derivative thereof; a GFP from another species such as *Renilla reniformis, Renilla mulleri,* or *Ptilosarcus guernyi*, as described in, e.g., WO 99/49019 and Peelle et al. (2001) *J Protein Chem.* 20:507-519; any of a variety of fluorescent and colored proteins from Anthozoan species, as described in, e.g., Matz et al. (1999) *Nature Biotechnol.* 17:969-973; and the like.

In some embodiments, the suicide substrate will be reversibly immobilized on an insoluble support, to facilitate isolation of the enzyme which is covalently modified with the suicide substrate. See, e.g., U.S. Pat. No. 5,571,681. Suitable insoluble supports include, but are not limited to, agarose (e.g., agarose beads), sepharose, glass, plastic (e.g., any of a group of synthetic or natural organic materials that may be shaped when soft and then hardened, including many types of resins, resinoids, polymers, cellulose derivatives, casein materials, and proteins), polypropylene, polystyrene, polystyrene beads, magnetic particles, other microparticles, polystyrene multiwell plates, polypropylene multiwell plates, polycarbonate multiwell plates, and the like. Insoluble supports can take any of a variety of forms, including, but not limited to, beads (which can be spherical, roughly spherical, or irregular in shape), plates, columns, and the like. Plates include multi-well plates (e.g., polystyrene or polypropylene plates) such as multi-well 96-well plates, 384-well plates, 1536-well plates, and the like.

In some embodiments, the suicide substrate is reversible linked to an insoluble support via a polymer matrix. See, e.g., U.S. Pat. No. 6,825,032 for a description of various polymers. Suitable polymer matrices include, but are not limited to, cellulose-based products such as hydroxyethyl cellulose, hydroxypropyl cellulose, carboxymethyl cellulose, cellulose acetate and cellulose butyrate, acrylics such as those polymerized from hydroxyethyl acrylate, hydroxyethyl methacrylate, glyceryl acrylate, glyceryl methacrylate, acrylic acid, methacrylic acid, acrylamide and methacrylamide, vinyls such as polyvinyl pyrrolidone and polyvinyl alcohol, nylons such as polycaprolactam, polylauryl lactam, polyhexamethylene adipamide and polyhexamethylene dodecanediamide; polyurethanes, polylactic acids, linear polysaccharides such as amylose, dextran, chitosan, heparin and hyaluronic acid, and branched polysaccharides such as amylopectin, hyaluronic acid and hemi-celluloses. Blends of two or more different polymer molecules can be used. For example, in one embodiment the polymer molecules are a mixture of dextran and heparin. In another embodiment dextran is mixed with poly Lys-Gly (1 lysine per 20 glycine). Polymers may be either natural or synthetic polymers and modified natural or modified synthetic polymers. The polymers may also be dextran polymers. Natural polymers are branched or linear polymers produced in a biological system. Examples of natural polymers include but are not limited to oligosaccharides, polysaccharides, peptides, proteins, glycogen, dextran, heparin, amylopectin, amylose, pectin, pectic polysaccharides, starch, DNA, RNA, and cellulose.

Synthetic polymers are branched or linear polymers that are manmade. Examples of synthetic polymers include plastics, elastomers, and adhesives, oligomers, homopolymers and copolymers produced as a result of addition, condensation or catalyst driven polymerization reactions, i.e., condensation polymerization. Modified natural polymers are natural polymers that have been chemically modified. Chemical modifications can be performed by, oxidation, or the covalent attachment of photo-reactive groups, affinity ligands, ion exchange ligands, hydrophobic ligands, other natural or synthetic polymers, and spacer molecules. Modified synthetic polymers are synthetic polymers that have been chemically modified. Chemical modifications can be done by, but are not limited to, oxidation, or the covalent attachment of photoreactive groups, affinity ligands, ion exchange ligands, hydrophobic ligands, or other natural or synthetic ligands.

The suicide substrate is in some embodiments "reversibly" immobilized on an insoluble support, e.g., after the enzyme is covalently modified with the suicide substrate, such that the covalently modified enzyme is immobilized on the insoluble support, the covalently modified substrate is released from the insoluble support. Release of the covalently modified substrate from the insoluble support is accomplished in a manner that will depend in part on the manner in which the suicide substrate is associated with the insoluble support. In some embodiments, the covalently modified substrate will be released from the insoluble support by contacting the immobilized covalently modified enzyme with a reducing agent. In other embodiments, the covalently modified substrate will be released from the insoluble support by altering the pH such that the covalently modified enzyme is released from the insoluble support.

Sources of Enzymes

Suitable sources of enzymes include, but are not limited to, a cell or organism of any of the six kingdoms, e.g., Bacteria (e.g., Eubacteria); Archaebacteria; Protista; Fungi; Plantae; and Animalia. Suitable sources of enzymes include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., Euglena), amoeboids (e.g., amoeba), sporozoans (e.g, Apicomplexa, Myxozoa, Microsporidia), and ciliates (e.g., Paramecium). Suitable sources of enzymes include members of the kingdom Fungi, including, but not limited to, members of any of the phyla: Basidiomycota (club fungi; e.g., members of Agaricus, Amanita, Boletus, Cantherellus, etc.); Ascomycota (sac fungi, including, e.g., Saccharomyces); Mycophycophyta (lichens); Zygomycota (conjugation fungi); and Deuteromycota. Suitable sources of enzymes include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sources of enzymes include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Thus, e.g., suitable cells include cells from organisms that include, but are not limited to, a protozoan, a plant, a fungus, algae, yeast, a reptile, an amphibian, a mammal, a marine microorganism, a marine invertebrate, an arthropod, an isopod, an insect, an arachnid, an archaebacterium, and a eubacterium.

Suitable prokaryotic cells include bacteria (e.g., Eubacteria) and archaebacteria. Suitable archaebacteria include a methanogen, an extreme halophile, an extreme thermophile, and the like. Suitable archaebacteria include, but are not limited to, any member of the groups Crenarchaeota (e.g., *Sulfolobus solfataricus, Defulfurococcus mobilis, Pyrodictium occultum, Thermofilum pendens, Thermoproteus tenax*), Euryarchaeota (e.g., *Thermococcus celer, Methanococcus thermolithotrophicus, Methanococcus jannaschii, Methanobacterium thermoautotrophicum, Methanobacterium formicum, Methanothermus fervidus, Archaeoglobus fulgidus, Thermoplasma acidophilum, Haloferax volcanni, Methanosarcina barkeri, Methanosaeta concilli, Methanospirillum hungatei, Methanomicrobium mobile*), and Korarchaeota. Suitable eubacteria include, but are not limited to, any member of Hydrogenobacteria, Thermotogales, Green nonsulfphur bacteria, Denococcus Group, Cyanobacteria, Purple bacteria, Planctomyces, Spirochetes, Green Sulphur bacteria, Cytophagas, and Gram positive bacteria (e.g., *Mycobacterium* sp., *Micrococcus* sp., *Streptomyces* sp., *Lactobacillus* sp., *Helicobacterium* sp., *Clostridium* sp., *Mycoplasma* sp., *Bacillus* sp., etc.).

In some embodiments, the source of enzyme will be a tissue taken from an organism; from a particular cell or group of cells isolated from an organism; etc. For example, where the organism is a plant, the source of enzyme will in some embodiments be isolated from the xylem, the phloem, the cambium layer, leaves, roots, etc. Where the organism is an animal, the source of enzyme will in some embodiments be isolated from a particular tissue (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some embodiments, the source of the enzyme will be taken from a consortium of organisms. For example, the source of the enzyme will in some embodiments be isolated from a mixture of soil microorganisms; a mixture of marine organisms; a mixture of lichen; and the like. In some embodiments, the source of the enzyme will be taken from a marine animal which is associated with various other organisms. For example, the source of the enzyme may be taken from a sponge which lives in the presence of many types of microorganisms within its structure. In some embodiments, the source of an enzyme will be a mixture of two or more organisms. In some embodiments, the two or more organisms are living in a symbiotic, or other type of relationship, with one another.

Cells, either unicellular organisms or cells isolated from a multicellular organism, and multicellular organisms, will in some embodiments be exposed to one or more internal or external signals before use of the cell or the organism as a source of enzyme. External and internal signals that affect gene expression and/or affect production of a given enzyme include, but are not limited to, infection of a cell by a microorganism, including, but not limited to, a bacterium (e.g., *Mycobacterium* spp., *Shigella, Chlamydia*, and the like), a protozoan (e.g., *Trypanosoma* spp., *Plasmodium* spp., *Toxoplasma* spp., and the like), a fungus, a yeast (e.g., *Candida* spp.), or a virus (including viruses that infect mammalian cells, such as human immunodeficiency virus, foot and mouth disease virus, Epstein-Barr virus, and the like; viruses that infect plant cells; etc.); infection of a plant with an insect (e.g., a spider mite, an aphid, a tobacco worm, etc.); withholding of water (e.g., withholding water from a plant); stress; infection of a plant with an arachnid; a wound (e.g., wounding a plant leaf, stem, or root); change in pH of the medium in which a cell is maintained or a change in internal pH; excessive heat relative to the normal range for the cell or the multicellular organism; excessive cold relative to the normal range for the cell or the multicellular organism; an effector molecule such as a hormone, a cytokine, a chemokine, a neurotransmitter; an ingested or applied drug; a ligand for a cell-surface receptor; a ligand for a receptor that exists internally in a cell, e.g., a nuclear receptor; hypoxia; light; dark; mitogens, including, but not limited to, lipopolysaccharide (LPS), pokeweed mitogen; antigens; sleep pattern; electrical charge; ion concentration of the medium in which a cell is maintained or an internal ion concentration, exemplary ions including sodium ions, potassium ions, chloride ions, calcium ions, and the like; presence or absence of a nutrient; metal ions; a transcription factor; a tumor suppressor; cell-cell contact; and the like.

Sample Processing

In some embodiments, a sample containing an enzyme is a crude lysate or homogenate. In other embodiments, a sample containing an enzyme is manipulated in various ways to purify the enzyme. Processing of a protein extract or other composition containing the covalently modified enzyme can be performed using methods well known in the art, including but not limited to, chromatography (high performance liquid chromatography, fast protein liquid chromatography, size exclusion chromatography, and the like), electrophoresis (e.g., two-dimensional gel electrophoresis), protein precipitation, and centrifugation. An enzyme can be isolated before or after covalent modification.

There are a variety of chromatographic approaches which may be used for fractionating complex protein mixtures in order to make them more manageable for mass spectrometric analysis. These rely on separation by size, charge, hydrophobicity, or other physical properties.

After chromatographic separation, the proteins will in some embodiments be further separated and/or treated for mass spectrometry. This preparation for mass spectrometry can be accomplished in a number of ways. The samples may be separated by one-dimensional or two-dimensional electrophoresis. In one-dimensional electrophoresis, gels are run according to methods well known in the art, such as the use of a BioRad mini gel system with pre cast acrylamide gels. In the two-dimensional electrophoresis, eluted proteins are diluted into a sample solubilization buffer comprised of 7M urea, 2M thiourea, 30 mM dithiothreitol (DTT), and 0.5% Triton X-100. The first dimension for isoelectric focusing (IEF) is carried out on a BioRad IPG system essentially as described by the manufacturer. Immobilized pH gradient strips are run for 30-45K volt hours. Prior to loading the IEF strips on the second dimension, the strips are re-equilibrated with a solution (2% SDS, 50 mM Tris, pH 6.9, 10% glycerol, and 7 mM urea) and directly applied to a BioRad 8-16% gradient sodium dodecyl sulfate-polyacrylamide gel electrophoresis (SDS-PAGE) gel for electrophoresis. The resultant gels are stained with silver or Sypro ruby, according to methods well established in the art. Protein spots are cut from the gel either manually or by using a robotic gel excision system.

It will be appreciated that two-dimensional preparative electrophoresis is not limited to isoelectric focusing followed by gradient gel electrophoresis. For example, other two-dimensional gel approaches can also be employed, such as blue native electrophoresis followed by PAGE or non-reducing PAGE followed by reducing SDS-PAGE. Two-dimensional gel electrophoresis has been amply described in a variety of publications; see, e.g., Shevchenko et al. (1996) *Proc. Natl. Acad. Sci. USA* 93:1440-1445.

In many embodiments, the covalently modified enzyme is purified (e.g., free from other contaminants, such as other macromolecules), such that it is at least about 50% pure, at least about 60% pure, at least about 70% pure, at least about 80% pure, at least about 85% pure, at least about 90% pure, at least about 95% pure, at least about 98% pure, at least about 99% pure, or greater than 99% pure.

Following purification of the covalently modified enzyme, the amino acid sequence of at least a portion of the covalently modified enzyme is determined. In some embodiments, the covalently modified enzyme is proteolytically cleaved into fragments (as described below); and the amino acid sequence of one or more of the fragments is determined. In many embodiments, the peptides are separated from one another (e.g., by a gel electrophoresis, a liquid chromatography, or other well-established separation technique) before being subjected to an amino acid sequencing technique.

In many embodiments, as discussed above, a suicide substrate is radiolabelled. After contacting a test sample (e.g., a biological sample) with a radiolabelled suicide substrate, where the contacting provides for covalent binding of the substrate to an amino acid of the enzyme to form a covalently modified, radiolabelled enzyme, the sample is subjected to one or more purification steps, to isolate (e.g., purify) the radiolabelled, covalently modified enzyme. Suitable purification steps include, but are not limited to, size exclusion chromatography, electrophoresis (e.g., two-dimensional gel electrophoresis), liquid chromatography (e.g., high performance liquid chromatography, fast protein liquid chromatography), and the like.

Following purification of the covalently modified, radiolabelled enzyme, the amino acid sequence of at least a portion of the covalently modified, radiolabelled enzyme is determined. In some embodiments, the covalently modified, radiolabelled enzyme is proteolytically cleaved into fragments (as described below); and the amino acid sequence of one or more of the fragments is determined. In many embodiments, the peptides are separated from one another (e.g., by a gel electrophoresis, a liquid chromatography, or other well-established separation technique) before being subjected to an amino acid sequencing technique.

Generation of Peptides

A covalently modified enzyme is subjected to one or more enzymatic digestion reactions, to generate peptides. Suitable peptides generally have a length of from about 2 amino acids to about 100 amino acids, e.g., from about 2 amino acids to about 5 amino acids, from about 5 amino acids to about 10 amino acids, from about 10 amino acids to about 15 amino acids, from about 10 amino acids to about 20 amino acids, from about 20 amino acids to about 25 amino acids, from about 25 amino acids to about 30 amino acids, from about 30 amino acids to about 40 amino acids, from about 40 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, or from about 90 amino acids to about 100 amino acids.

Suitable proteolytic enzymes are known in the art and include, but are not limited to, trypsin, pepsin, chymotrypsin, papain, bromelain, elastase, carboxypeptidase A, carboxypeptidase B, carboxypeptidase P, carboxypeptidase Y, thermolysin, thrombin, rennin, subtilisin, and the like. In some embodiments, a covalently modified enzyme is fragmented using trypsin. In other embodiments, a covalently modified enzyme is fragmented using pepsin. In other embodiments, a covalently modified enzyme is fragmented using chymotrypsin.

In some embodiments, a covalently modified enzyme is fragmented using a first proteolytic enzyme, generating a first set of proteolytic fragments; and the first set proteolytic fragments is subjected to tandem mass spectrometry or other protein sequencing method; the covalently modified enzyme is fragmented using a second proteolytic enzyme, generating a second set of proteolytic fragments; and the second set of proteolytic fragments is subjected to tandem mass spectrometry or other protein sequencing method. In this way, overlapping peptides are generated, e.g., peptides that overlap the first set, and allow ordering of the peptides. In some embodiments, the covalently modified enzyme is fragmented using a third proteolytic enzyme, generating a third set of proteolytic fragments; and the third set of proteolytic fragments is subjected to tandem mass spectrometry or other protein sequencing method. The first, second, third, etc., proteolytic enzymes are selected from any known proteolytic enzymes, including those discussed above.

In some embodiments, overlapping peptides are generated. Overlapping peptides can be generated using well-established techniques. For example, in separate reactions, a covalently modified enzyme is digested with trypsin for varying amounts of time, generating a series of overlapping peptides. As another example, a covalently modified enzyme is digested, in separate reactions, with two or more different proteolytic enzymes.

Separation of Peptides

In some embodiments, an enzyme that is covalently modified according to a subject method, and/or peptides generated from a covalently modified enzyme, is subjected to one or more dimensional chromatography. In some embodiments, peptides are separated using a high performance liquid chromatography column comprising a strong anion exchange resin followed by a reverse phase resin. In some embodiments, peptides are separated using fast protein liquid chromatography. In some embodiments, peptides are separated using two-dimensional gel electrophoresis.

In an alternative embodiment, preparative treatment of proteins prior to mass spectrometry or other protein sequencing method analysis relies on further chromatographic separation of peptide fragments generated by proteolysis of the proteins. The resultant peptide mixture can be subjected to one- or multi-dimensional chromatography column prior to mass spectrometry analysis or other protein sequencing method.

In certain embodiments, a two-dimensional high performance liquid chromatography (HPLC) column comprising a strong anion exchange resin stacked adjacent to a reverse-phase resin is contemplated. The peptide mixture is first subjected to the anion exchanger then subsequently to the hydrophobic interaction resin.

In many embodiments, as discussed above, a suicide substrate is radiolabelled. After contacting a test sample (e.g., a biological sample) with a radiolabelled suicide substrate, where the contacting provides for covalent binding of the substrate to an amino acid of the enzyme to form a covalently modified enzyme, the sample is subjected to one or more purification steps, to isolate the radiolabelled, covalently modified enzyme. Suitable purification steps include, but are not limited to, size exclusion chromatography, electrophoresis (e.g., two-dimensional gel electrophoresis), liquid chromatography (e.g., high performance liquid chromatography, fast protein liquid chromatography), and the like.

Amino Acid Sequence Determination

Any known amino acid sequencing method can be used to determine the amino acid sequence of at least a portion of a covalently modified enzyme. In many embodiments, as discussed above, the covalently modified enzyme is purified; the covalently modified enzyme is fragmented into peptides; and amino acid sequence of the covalently modified peptide is determined.

In some embodiments, the amino acid sequence of the peptide comprising an amino acid that is covalently modified by the suicide substrate is determined. In some of these embodiments, the peptide comprising the covalently modified amino acid residue comprises from about one amino acid to about 20 amino acids (e.g., from about one amino acid to about 5 amino acids, from about 5 amino acids to about 10 amino acids, from about 10 amino acids to about 15 amino acids, or from about 15 amino acids to about 20 amino acids) on the amino terminal side and/or on the carboxyl-terminal side of the covalently modified amino acid residue.

In some embodiments, in addition to determining the amino acid sequence of the peptide comprising the amino acid residue covalently modified by the selected suicide substrate, one or more additional peptides that are generated by proteolytic cleavage of the protein are determined.

Suitable methods for determining an amino acid sequence of the covalently modified peptide include, but are not limited to, Edman degradation; tandem mass spectrometry; and the like. See, Edman, P., "Sequence Determination", *Mol. Biol. Biochem. Biophys.*, (1970), 8:211-255; U.S. Pat. No. 6,799,121 (amino acid sequencing using tandem mass spectrometry).

The amino acid sequence of the peptide(s) is compared to amino acid sequences of known proteins. In many embodiments, an enzyme identified using a subject method is a previously unidentified (e.g., a previously unreported) and/or previously uncharacterized enzyme; and is in many embodiments a previously unisolated enzyme.

Tandem Mass Spectrometry

The term "mass spectrometry" is used herein in its usual sense to include various methods such as tandem mass spectrometry, matrix assisted laser desorption ionization (MALDI) time-of-flight (TOF) mass spectrometers (MS), MALDI-TOF-TOF MS, MALDI Quadrupole-time-of-flight (Q-TOF) MS, electrospray ionization (ESI)-TOF MS, ESI-Q-TOF, ESI-TOF-TOF, ESI-ion trap MS, ESI Triple quadrupole MS, ESI Fourier Transform Mass Spectrometry (FTMS), MALDI-FTMS, MALDI-Ion Trap-TOF, and ESI-Ion Trap TOF. These mass spectrometry methods are well known in the art, see e.g., Chapters 1-4 etc. of Gary Siuzdak, "Mass Spectrometry for Biotechnology," Academic Press, N.Y., (1996). At its most basic level, mass spectrometry involves ionizing a molecule and then measuring the mass of the resulting ion. Since molecules ionize in a way that is well known, the molecular weight of the molecule can generally be accurately determined from the mass of the ion.

Tandem mass spectrometry has been used to identify proteins because it can provide information in addition to parent ion molecular weight. Tandem mass spectrometry involves first obtaining a mass spectrum of the ion of interest, then fragmenting that ion and obtaining a mass spectrum of the fragments. Tandem mass spectrometry thus provides both molecular weight information and a fragmentation pattern that can be used in combination along with the molecular weight information to identify the exact sequence of the peptide. Hunt et al. (1986) *Proc. Natl. Acad. Sci. USA* 83:6233-6237; Johnson et al. (1988) *Int. J. Mass Spectrom. Ion Processes* 86:137-154; Papayannopoulos (1995) *Mass Spectrom. Rev.* 14:49-73; Shevchenko et al. (1996) *Proc. Natl. Acad. Sci. U.S.A.* 93:14440-14445; Figeys et al. (1996) *Anal. Chem.* 68:1822-1828; and Wilm et al. (1996) *Nature* 379:466-469.

Any mass spectrometers that are capable of tandem mass spectrometry, e.g., two triple quadrupole mass spectrometers, a quadrupole/time-of-flight mass spectrometer, an ion-trap mass spectrometer, or a time-of-flight mass spectrometer amenable to post-source decay or collision-induced dissociation, may be used, with appropriate adjustments known to those skilled in the art. The ions may be generated by a number of methods including electrospray, MALDI (matrix-assisted laser desorption ionization) and FAB (fast-atom bombardment). The method of the invention can be applied to oligopeptides of any length, preferably the number of amino acid residues is between 3 and 20.

Mass spectrometry has become the method of choice for the sequencing and identification of proteins due to its speed, sensitivity, and the quality of data generated in the analysis. Multiple proteins can be identified or sequenced per hour, often resulting in 50-90% protein sequence coverage for a single tryptic digest. Multiple digests can yield 100% coverage with femtomole quantities of sample; attomole sensitivities are obtainable with careful tuning of the instrument. These methods, developed for purified protein samples, hold promise for analyzing complex protein mixtures.

De novo protein sequencing requires at least one purification step and a proteolytic digestion that allows the sequencing of multiple short peptide fragments. Generally, proteins are separated by SDS-polyacrylamide gel electrophoresis (PAGE) or 2D gel electrophoresis. Proteins of interest are identified on the gel, eluted from the gel, reduced and alkylated to prevent the formation of mixed disulfides, and digested with a proteolytic enzyme, usually trypsin. Eluted peptides can then separated by liquid chromatography (LC) and analyzed by tandem MS. Peptide ions, created through either electrospray ionization or matrix assisted laser desorption/ionization (MALDI) are analyzed by a first stage MS to give the mass to charge ratio (m/z) of the initial peptide. In tandem MS, single peptide ions identified by the first MS, are selected and fragmented through collision with a neutral gas. The ion products of this fragmentation can be analyzed in the second stage of mass analysis. Peptide ions most commonly fragment at the amide bond, creating ions in which the charge is retained on the N-terminus (b-ions) or the C-terminus (y-ions). The peptide sequence can be deduced from the differences in the b- and y-ion series.

Software packages accompanying tandem MS systems are able to sequence peptides co-eluting from an LC unit using automated exclusion strategies. This exclusion strategy prevents the second (sequencing) stage of MS for peptides of a specific mass that have already been sequenced. Such exclusion strategies generally allow for the simultaneous sequencing of 4 peptides over the length of an eluting LC peak (30-90 seconds). Exclusion lists can also be built automatically for entire chromatographic runs by specifying elution time and peptide m/z, allowing for the sequencing of more co-eluting peptides through multiple chromatographic runs.

Determining Nucleic Acid Sequences

The present invention provides methods for identifying nucleic acids encoding enzymes having particular enzymatic activities, the methods generally involving identifying an enzyme, as described above, and, based on the amino acid sequence of at least a portion of the enzyme, designing degenerate nucleotide sequences encoding the amino acid sequence. The nucleic acids comprising degenerate nucleotide sequences are useful as probes, to identify longer nucleic acids that encode the enzyme; and are useful as "primers," to initiate DNA polymerase-catalyzed synthesis of a nucleic acid using a complementary DNA strand as a template.

Those skilled in the art are familiar with methods of designing degenerate nucleotide sequences encoding an amino acid sequence. Degenerate primers are a set of primers which have a number of options at several positions in the sequence, based on the degeneracy of the genetic code. For example, leucine is encoded by CTA, CTG, CTT, or CTC; serine is encoded by TCA, TCG, TCT, or TCC; arginine is encoded by CGA, CGG, CGT, or CGC; glycine is encoded by GGA, GGG, GGT, or GGC; proline is encoded by CCA, CCG, CCT, or CCC; alanine is encoded by GCA, GCG, GCG, or GCC; etc. The following is a non-limiting example of a degenerate primer: NCCYAAYTGNCCNT, where Y=T+C, and N=A+G+C+T. Primers with as high as 256- and 1024-fold degeneracy have been used for the successful amplification and subsequent direct sequencing of a wide range of nucleic acids, e.g., viral nucleic acids.

In many embodiments, nucleic acids with degenerate nucleotide sequences are from about 10 nucleotides to about 100 nucleotides in length, e.g., from about 10 nucleotides to about 15 nucleotides, from about 10 nucleotides to about 20 nucleotides, from about 15 nucleotides to about 25 nucleotides, from about 20 nucleotides to about 30 nucleotides, from about 25 nucleotides to about 35 nucleotides, from about 30 nucleotides to about 40 nucleotides, from about 35 nucleotides to about 45 nucleotides, from about 40 nucleotides to about 50 nucleotides, from about 45 nucleotides to about 55 nucleotides, from about 50 nucleotides to about 60 nucleotides, from about 55 nucleotides to about 65 nucleotides, from about 60 nucleotides to about 70 nucleotides, from about 65 nucleotides to about 75 nucleotides, from about 70 nucleotides to about 80 nucleotides, from about 75 nucleotides to about 85 nucleotides, from about 80 nucleotides to about 90 nucleotides, from about 85 nucleotides to about 95 nucleotides, or from about 90 nucleotides to about 100 nucleotides in length.

As discussed above, synthetic nucleic acids comprising degenerate nucleotide sequences are useful as nucleic acid probes to identify nucleic acids that comprise nucleotide sequences encoding an enzyme (e.g., an enzyme identified in a subject method). For example, the synthetic nucleic acid can be used to identify a longer nucleic acid, e.g., an mRNA, a cDNA, a genomic DNA, and the like. The source of the mRNA, a cDNA, a genomic DNA, etc., can be the same as that described above for the source of the enzyme. Procedures for nucleic acid hybridization are well known in the art. In many embodiments, the nucleic acid probe will be detectably labeled. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA); radioactive labels, e.g. $^{32}$P, $^{35}$S, $^{3}$H; etc. In some embodiments, the nucleic acid hybridization will be conducted under stringent hybridization conditions.

As discussed above, synthetic nucleic acids comprising degenerate nucleotide sequences are useful as primers, to initiate DNA polymerase-catalyzed synthesis of a nucleic acid strand based on a nucleic acid template. Suitable nucleic acid template includes mRNA (e.g., a cDNA copy of mRNA), and genomic DNA. The source of the mRNA, a cDNA, a genomic DNA, etc., can be the same as that described above for the source of the enzyme. In many embodiments, one or more of the nucleic acid primers will be detectably labeled. Detectable labels include fluorochromes and radiolabels, as discussed above.

In some embodiments, the primers will be used to initiate multiple rounds of synthesis, in a polymerase chain reaction. Those skilled in the art are well aware of polymerase chain reaction conditions. Conditions that permit primer-initiated nucleic acid amplification are well known to those skilled in the art, and include the presence of a DNA polymerase; deoxynucleotide triphosphates; and magnesium ions. Suitable reaction conditions are well known to those skilled in the art of nucleic acid amplification. Exemplary, non-limiting reaction conditions are described in the Examples. The DNA polymerase is generally one that has high affinity for binding at the 3'-end of an oligonucleotide hybridized to a nucleic acid strand. The DNA polymerase is generally one that has little or no 5'→3' exonuclease activity so as to minimize degradation of primer, termination or primer extension polynucleotides. The DNA polymerase is generally one that has little to no proofreading activity. In many embodiments, the DNA polymerase is thermostable, e.g., is catalytically active at temperatures in excess of about 75° C. DNA polymerases that are suitable for use in a subject method include, but are not limited to, DNA polymerases discussed in U.S. Pat. Nos. 5,648,211 and 5,744,312, which include exo⁻ Vent (New England Biolabs), exo⁻ Deep Vent (New England Biolabs), Bst (BioRad), exo⁻ Pfu (Stratagene), Bca (Panvera), sequencing grade Taq (Promega); thermostable DNA polymerases from *Thermoanaerobacter thermohydrosulfuricus*; and the like. In some embodiments, the reaction mixture includes an RNAse H.

Magnesium ions are typically present in the reaction mix in a concentration of from about 1 mM to about 100 mM, e.g., from about 1 mM to about 3 mM, from about 3 mM to about 5 mM, from about 5 mM to about 10 mM, from about 10 mM to about 25 mM, from about 25 mM to about 50 mM, from about 50 mM to about 75 mM, or from about 75 mM to about 100 mM.

Usually the reaction mixture will comprise four different types of dNTPs corresponding to the four naturally occurring bases are present, i.e. dATP, dTTP, dCTP and dGTP. In the subject methods, each dNTP will typically be present in an amount ranging from about 10 to 5000 μM, usually from about 20 to 1000 μM, e.g., 100 nM-200 nM.

The reaction mixture prepared in the first step of the subject methods further includes an aqueous buffer medium that includes a source of monovalent ions, a source of divalent cations and a buffering agent. Any convenient source of monovalent ions, such as KCl, K-acetate, NH$_4$-acetate, K-glutamate, NH$_4$Cl, ammonium sulfate, and the like may be employed. The divalent cation may be magnesium, manganese, zinc and the like, where the cation will typically be magnesium. Any convenient source of magnesium cation may be employed, including MgCl$_2$, Mg-acetate, and the like. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, e.g., pH 7.3 at 72° C. Exemplary conditions are 10-50 mM Tris-HCl at pH 8.3. Other agents which may be present in the buffer medium include chelating agents, such as EDTA, EGTA and the like; gelatin or bovine serum albumin to 100 μg/ml, and/or non-ionic detergents such as Tween-20 or Nonidet P-40 or Triton X-100 (0.05-0.10% v/v).

Subject synthetic nucleic acids comprising degenerate nucleotide sequences are also useful for in silico analysis, e.g., to query a genomic or cDNA sequence library. The genomic or cDNA sequence library generated from the source of the enzyme is compared to the degenerate primer sequence to determine possible matching sequences, thus leading to the complete nucleotide sequence of the nucleic acid encoding the enzyme.

Thus, the present invention provides synthetic nucleic acids, which comprise degenerate nucleotide sequences; as well as isolated nucleic acids identified by a subject synthetic nucleic acid; as well as synthetic nucleic acids amplified in vitro using subject synthetic nucleic acid primers. Isolated nucleic acids such as cDNAs and genomic DNAs, as well as amplified nucleic acids, are cloned into appropriate vectors for propagation and/or expression (e.g., production of the encoded enzyme in a host cell genetically modified with the nucleic acid). Thus, also provided are constructs ("recombinant vectors") comprising the subject nucleic acids inserted into a vector, and host cells comprising the constructs.

The subject constructs are used for a number of different applications, including propagation, enzyme production, etc. Viral and non-viral vectors may be prepared and used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal. The choice of appropriate vector is well within the skill of the art. Many such vectors are available commercially.

To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the identified enzymes. For expression, the gene product encoded by a polynucleotide of the invention is expressed in any convenient expression system, including, for example, bacterial, yeast, insect, amphibian, and mammalian systems. Suitable vectors and host cells are described in U.S. Pat. No. 5,654, 173.

In the expression vector, an enzyme-encoding polynucleotide is operably linked to a regulatory sequence as appropriate to obtain the desired expression properties. These can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific, or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the enzyme-coding gene, or may be derived from exogenous sources.

Expression vectors generally have convenient restriction sites located near the promoter sequence to provide for the insertion of nucleic acid sequences encoding heterologous proteins. A selectable marker operative in the expression host may be present, for detection of host cells that comprise the recombinant vector. A variety of markers are known and may be present on the vector, where such markers include those that confer antibiotic resistance, e.g. resistance to ampicillin, tetracycline, chloramphenicol, kanamycin, neomycin; markers that provide for histochemical detection, etc. Expression vectors may be used for, among other things, the production of subject proteins, subject fusion proteins, as described above, and for use in screening assays, as described below.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, or for use in screening assays as described herein, a unicellular organism, such as *E. coli*, *B. subtilis*, *S. cerevisiae*, insect cells in combination with baculovirus vectors, or cells of a higher organism such as vertebrates, e.g. COS 7 cells, HEK 293, CHO, *Xenopus oocytes*, lepidopteran Sf-9 or S-21 cells, *Drosophila* S2 cells, may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci. (USA)* (1983) 80:21-25; and Siebenlist et al., *Cell* (1980) 20:269.

Yeast. Expression systems in yeast include those described in Hinnen et al., *Proc. Natl. Acad. Sci. (USA)* (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al., *Proc. Natl. Acad. Sci. (USA)* (1984) 81:1470-1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci. (USA)* (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594. Various insect cells, including lepidopteran Sf-9 cells and S-21 cells, and *Drosophila* S2 cells, have been amply described in the art. See, e.g., "Insect Cell Culture Engineering", Goosen, Daugulis, and Faulkner, eds. (1993) Marcel Dekker.

Mammalian Cells. Mammalian expression is accomplished as described in Dijkema et al., *EMBO J.* (1985) 4:761, Gorman et al., *Proc. Natl. Acad. Sci.* (USA) (1982) 79:6777, Boshart et al., *Cell* (1985) 41:521 and U.S. Pat. No. 4,399, 216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, and WO 87/00195.

Plant cells. Plant cell culture is amply described in various publications, including, e.g., *Plant Cell Culture: A Practical Approach*, (1995) R. A. Dixon and R. A. Gonzales, eds., IRL Press; and U.S. Pat. No. 6,069,009.

Following preparation of the expression vector, the expression vector will be introduced into an appropriate host cell for production of the subject polypeptide, i.e. a host cell will be transformed with the expression vector. Introduction of the recombinant vector into a host cell is accomplished in any convenient manner, including, but not limited to, calcium phosphate precipitation, electroporation, microinjection, use of lipids (e.g., lipofectin), infection, and the like.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

The exact function of the enzyme can then be determined in vitro and/or in vivo, using a system appropriate to the enzyme being detected. As one non-limiting example, where a subject method is carried out with a suicide substrate that is specific for terpene synthases, an in vivo biological system engineered to produce isoprenoids (e.g., as described in US Patent Publication No. 20030148479) can be used to determine the function of the enzyme. Alternatively, any well-established in vitro system for determining terpene synthase function can be used for determining the function of an enzyme detected using a subject method. See, e.g., Martin et al. *Nature Biotechnology* 21(7):796-802 (2003); Wang and Ohnuma (2000) *Biochim. Biophys. Acta* 1529:33-48; Trapp and Croteau (2001) *Genetics* 158:811-832; and Back and Chappell (1996) *Proc. Natl. Acad. Sci. USA* 93:6841-6845.

In many embodiments, an isolated nucleic acid comprising a nucleotide sequence encoding the enzyme identified using a subject method is inserted into an expression vector, generating a recombinant expression vector. A subject recombinant expression vector (comprising an isolated nucleic acid comprising a nucleotide sequence encoding the enzyme identified using a subject method) is then introduced into an appropriate host cell, generating a genetically modified host cell; the enzyme is then produced within the genetically modified host cell in quantities suitable for determination of its function.

Terpene Synthases

In some embodiments, a subject method provides for identification of previously unidentified terpene synthases. The first committed step in the biosynthesis of all terpenes is the cyclization of a universal isoprenoid precursor molecule by a terpene synthase. The primary building block ($C_5$ unit) for terpenes is isopentenyl diphosphate (IPP). IPP is synthesized via two different pathways: the mevalonate pathway and the non-mevalonate, or 1-deoxyxylulose-5-phosphate (DXP) pathway (FIG. 1). The mevalonate pathway is found primarily in eukaryotes and archaea, whereas the DXP pathway is found primarily in prokaryotes, such as *E. coli*, and plastid organelles. Prenyltransferases catalyze the sequential additions of IPP to its allylic isomer dimethylallyl diphosphate (DMAPP) to form $C_{10}$ geranyl diphosphate (GPP), $C_{15}$ farnesyl diphosphate (FPP), $C_{20}$ geranylgeranyl diphosphate (GGPP), and larger isoprenyl diphosphates. Amino acid substitutions near the active site can change the product distribution of the enzyme so that an FPP synthase can be engineered to produce either GPP or GGPP. Cyclization of GPP, FPP, or GGPP by terpene synthases forms monoterpenes, sesquiterpenes, or diterpenes, respectively. All terpene synthases share a similar reaction mechanism catalyzing an intramolecular reaction of polyprenyl diphosphates.

Thus, in some embodiments, the instant invention provides a method for identifying a terpene synthase in a biological sample. The method generally involves contacting the sample with a synthetic suicide substrate, where the contacting results in covalent binding of the suicide substrate to an amino acid in the terpene synthase, forming a covalently modified terpene synthase; and determining the amino acid sequence of at least a portion of the covalently modified terpene synthase. The amino acid sequence of the active site is used to design degenerate nucleic acid primers, for use in amplifying a nucleic acid that encodes the terpene synthase.

In some aspects, a subject method for identifying a terpene synthase involves contacting a sample containing a terpene synthase with a synthetic suicide substrate, where the contacting results in covalent binding of the suicide substrate to an amino acid in the terpene synthase, forming a covalently modified terpene synthase; identifying the covalently modified terpene synthase through a tag mass shift signature using mass spectrometry; and reconstructing the terpene synthase amino acid sequences from constituent peptides sequenced by tandem-mass spectrometry or by N-terminal sequencing of the peptides of the synthase.

In one aspect, the instant invention provides to a method for identifying a nucleic acid comprising a nucleotide sequence that encodes a terpene synthase. The method involves determining the amino acid sequence of at least a portion of a terpene synthase active site, as discussed above; and using a nucleic acid designed based on the amino acid sequence of the terpene synthase active site to identify a nucleic acid that comprises a nucleotide sequence encoding a terpene synthase.

In some embodiments, the terpene synthase is a sesquiterpene synthase. In many of these embodiments, the active site of a terpene synthase is modified using the farnesyl diphosphate analog and a mechanistic inhibitor 10-cyclopropylidine farnesyl diphosphate (CP-FPP).

The present invention is a method for discovering and isolating new terpene synthase genes from diverse organisms and environmental samples. A mechanism-based enzyme "tagging" method is first used to identify terpene synthase enzymes, and tandem mass spectrometry (MS) is then used for the peptide sequencing of the "tagged" protein. Thus, the isolation and peptide sequencing of numerous sesquiterpene synthases using the farnesyl diphosphate analog and a mechanistic inhibitor such as 10-cyclopropylidine farnesyl diphosphate (CP-FPP).

Briefly, to identify new terpene synthases from an organism that is known to produce terpenes (e.g., sponges, coral, plants), synthases present in crude tissue extracts are specifically alkylated or chemically modified, i.e., "tagged", using a suitable suicide substrate. For example, cyclopropyl geranyl diphosphate (GDP), farnesyl diphosphate (FDP), and geranylgeranyl diphosphate (GGDP) analogs are available for use as mechanism-based inhibitors of terpene synthases. These inhibitors covalently modify terpene synthases by alkylating amino acid residues of the synthases.

The tagged enzyme is then enriched and then amino acid sequences of portions of the enzyme are determined by tandem MS or N-terminal sequencing. The gene sequence encoding the peptides are then degeneratively reconstructed from the peptide sequence(s). Full gene sequences can then be found using the degenerate gene sequences as probes against a cDNA or genomic DNA library. Since this gene discovery method is based upon enzymatic function rather than on sequence similarity, the method of the invention has the capability to identify a broader range of terpene synthases than is possible with current, homology-based methods by capitalizing on the fact that all synthases, though dissimilar at the sequence level, perform similar chemistries on specific substrates. The sequenced synthases can then be expressed in a terpene precursor over-producing strain to produce large quantities of biosynthetically-produced, high-value terpenoids.

Accordingly, one embodiment of the invention is a method for identifying a terpene synthase in a crude extract of whole cell material comprising: tagging terpene synthases present in the extract with a mechanism-based suicide substrate; separating and identifying the tagged synthase(s) through a tag mass shift signature using nano-liquid chromatography and mass spectrometry; and reconstructing the synthase sequences from constituent peptides sequenced by tandem-mass spectrometry.

As noted above, terpene synthase genes have been identified by use of known DNA, by the use of partial protein sequences from purified synthase enzymes and by the use of similarity-based PCR. The method of the invention provides for a unique combination of these techniques used in conjunction with state of the art tandem MS to determine the sequence synthase genes and clone these genes. Using this method, synthase genes can be cloned from a marine coral, which has not been achievable by current methodologies. To date, researchers have not been able to isolate synthase genes from animal sources using DNA sequences from plants and similarity-based methodologies. This is likely due to sequence dissimilarity between plant and animal synthases, which will not present an obstacle for the MS-based method.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

The practice of the present invention will employ, unless otherwise indicated, conventional techniques of synthetic organic chemistry, biochemistry, molecular biology, and the like, which are within the skill of the art. Such techniques are explained fully in the literature. See, for example, Sambrook, et al., *Molecular Cloning: A Laboratory Manual*, 2$^{nd}$ edition (1989); *Oligonucleotide Synthesis* (M. J. Gait, ed., 1984); *The Practice of Peptide Synthesis* (M. Bodanszky and A. Bodanszky, 2$^{nd}$ ed., Springer-Verlag, New York, N.Y., 1994); *Nucleic Acid Hybridization* (B. D. Haines & S. J. Higgins, eds., 1984); *Methods in Enzymology* (Academic Press, Inc.); Kirk-Othmer's *Encyclopedia of Chemical Technology*; and House's *Modern Synthetic Reactions*.

The following examples describe methods that provide for the cost-effective heterologous production of eleutherobin and sarcodictiyns in an *E. coli* host. The diterpene synthase responsible for the biosynthesis of eleutherobin and the sarcodictiyns in *Erythropodium caribaeorum* is first isolated. The identification of this terpene synthase provides a tool for the isolation of the enzymes responsible for further modification of the eleutherobin carbon backbone.

Cyclopropyl GGPP inhibitors are then used to isolate and sequence peptides from the terpene synthase responsible for the first step in the production of eleutherobin from GGPP. These peptide sequences are then used to design degenerate PCR primers to clone full length diterpene synthase genes from the coral sample. The genes are then expressed in an *E. coli* host to identify which synthase produces eunicellane.

In general, these experiments involve (1) confirming the presence of eleutherobin in the coral *E. caribaeorum* (or its associated symbionts) and extract protein and genomic DNA from the consortium; (2) "tagging" diterpene synthases using CP-GGPP analogs and sequence tagged tryptic peptides by LC-MS/MS using the peptide modification as a reference; (3) designing degenerate PCR primers from peptide sequences to isolate full length synthase gene sequence(s) by adapter-ligated PCR or cloning from a partial genomic library; and (4) expressing these sequences in an *E. coli* strain engineered to produce GGPP, determine the products formed by each synthesized diterpene synthase, and identify the synthase responsible for producing the eunicellane carbon skeleton found in eleutherobin. A flow-chart of these procedures is outlined in FIG. 3.

Example 1

Isolation of Eleutherobin, Nucleic Acids and Protein from Cultured *Erythropodium caribaeorum*

Approximately 2 kg of cultured *Erythropodium caribaeorum* is obtained from a commercial source, such as Ocean Dreams Inc. in Tampa, Fla. This is shipped in chilled seawater to retain the coral viability. This sample is divided and used for three purposes: 1) to verify the presence of eleutherobin within the sample, 2) to obtain genomic DNA and mRNA to be used in hybridization and PCR-based identification of terpene synthases, and 3) to obtain cell lysates to be used in the functionally-based covalent modification of diterpene synthases.

Eleutherobin Extraction

Eleutherobin is extracted from approximately 500 g of coral through a methanol extraction, as described in Taglialatela-Scafati et al. (2002) *Org Lett* 4(23):4085-8. Briefly, extracts are vacuum concentrated and hydrophobic organic compounds are back extracted with 50% v/w ethyl acetate. The organic layer is partitioned between hexane and 90% methanol in water, and the aqueous phase is collected. Eleutherobins are purified from the aqueous phase via elution from a normal-phase flash chromatography column at 6:4 n-hexane/ethyl acetate. The presence of eleutherobins is confirmed by UV absorbance at 290 nm (with log $\epsilon$ of approximately 4.0) and by liquid chromatography-mass spectrometry (LC-MS) analysis. These eleutherobins are separated using normal-phase high performance liquid chromatography (HPLC) on a silica column, eluting from $CH_2Cl_2$ to 30% MeOH in $CH_2Cl_2$, and identified using MS to confirm the expected molecular weights of eleutherobin ([M+H]+ at 656.3), desmethyleleutherobin (643.3), desacetyleleuterobin (615.3), and isoeleutherobin and z-eleutherobin (657.3).

Genomic DNA and Total RNA Preparation Genomic DNA and total RNA is prepared from the cultured *E. caribaeorum* and any associated symbionts. Total RNA from *E. caribaeorum* is prepared using a method designed for "difficult sources" such as the coral *Plexaura homomalla*, bark of yew tree and marine algae (Brash et al. (1996) *J Biol Chem* 271(34):20949-57). Genomic DNA is prepared using standard extraction techniques for soft marine tissue samples, as described in (Vibede et al. (1998) *Biochem Biophys Res Commun* 252(2):497-501).

Crude Enzyme Preparation

The acetone powder of the coral is prepared for use in enzyme assays. Approximately 100 g of coral is homogenized in a blender for 1 minute in cold (−20° C.) acetone. This mixture is centrifuged at 3000×g for 5 minutes at 4° C. and the residual solids are washed three times with cold acetone, discarding the supernatants. Protein is separated from any skeletal elements by swirling in cold acetone and decanting. The fine solids (expected to be approximately 10 g) are filtered and dried in a stream of argon and stored at −80° C. For use in enzyme assays, protein is solubilized from the powder by adding 5 mg per ml of 50 mM Tris-HCl pH 7.4.

Example 2

Functionally-Based Covalent Modifications of Diterpene Synthases in *Erythropodium caribaeorum* and its Symbionts In order to obtain probes specific for diterpene synthases in the coral sample, the terpene synthase inhibitors developed by Cane et al., supra, (specifically, CP-GGPP) are used to covalently modify all enzymes that cyclize GGPP. The inhibitor-tagged synthases are identified and the peptides that comprise the enzymes are sequenced using liquid chromatography-tandem mass spectrometry (LC tandem-MS) analysis, on Applied Biosystems QTRAP and QSTAR mass spectrometers.

Upon inspection of the eunicellane skeleton, the reaction mechanism is expected to be analogous to that of epi-cubenol and cadinene synthases (sesquiterpene synthases) (Benedict et al. (2001) *Plant Physiol* 125(4):1754-65). An initial ring closure at C1 to C14 would be followed by a migration of the carbocation from the C-15 position to the C-1 position due to a 1,3-hydride shift (FIG. 7). While the use of CP-GGPP was unsuccessful in covalently modifying and inhibiting taxadiene synthase (Williams et al. (2000) *Archives of Biochemistry and Biophysics* 379(1):137-146), the proposed mechanism for the eunicellane synthase differs significantly from that of taxadiene synthase. The presence of the cyclopropyl group in the inhibitor is expected to delocalize the carbocation from the C-15 position to the favored allylic C-16 and C-17 positions, making the enzyme unlikely to perform the 1,3 hydride shift, and thus unable to complete cyclization (FIG. 5). The carbocation retained on C16 or C17 would then be free to alkylate the synthase. In the case of taxadiene synthase, the mechanism of the enzyme is likely conserved when acting upon the CP-GGPP substrate, completing cyclization such that it does not modify the enzyme (Hale et al. (1998) *Protein Expr Purif* 12(2):185-8).

Conditions for the Functionally-Based Covalent Modification Reactions

Initial studies are performed using a purified diterpene synthase to determine the effects of the modification on the mass spectrometry of tagged peptides. The casbene and kaurene synthase genes have previously been cloned, and each enzyme is purified through expression as a His-tag fusion. An aliquot of each pure synthase is mixed in assay buffer with CP-GGPP. Each synthase is incubated at 30° C. for up to 12 hours with an excess amount of inhibitor to ensure complete inactivation and tagging of the enzyme after the 12 hour period. Proteins from these preparations are separated and analyzed according to the protocols detailed below to identify the covalently modified peptide and amino acid.

As a further control, purified diterpene synthase is added at differing concentrations to crude cell lysates of *E. coli* and the sample is exposed to the cyclopropyl inhibitor under similar reaction conditions. Using this labeled system, conditions for enrichment of tagged synthases are determined as detailed below.

Enrichment of Protein Samples Containing CP-GGPP Tagged Diterpene Synthases

Enrichment simplifies MS interpretation and aids in protein sequencing. Tagged synthases are partially purified or enriched using PAGE and HPLC techniques to separate tagged from non-tagged enzymes. Radio-labeled (tritiated) inhibitor is used to follow the separation of tagged synthases from crude cell lysate.

Gel Separation of Tagged Synthase

Crude cell lysate of an *E. coli* strain over-expressing a diterpene synthase is prepared by standard methods and exposed to 100 μM of the tritiated inhibitor. The crude enzyme preparation is separated by 1-D isoelectric focusing or 2D-gel electrophoresis, and the tagged enzyme(s) are identified as the radiolabeled spots using a Typhoon (Molecular Dynamics) multi-imager. Once spots are identified, the experiment is repeated using non-radiolabeled CP-GGPP to tag the synthases. Corresponding spots are excised, proteolyzed and extracted from the gel (Nakayama et al. (1996) *Journal of Chromatography A* 730(1-2):279-287). Resulting peptides are analyzed by tandem-MS.

Enrichment of Tagged Proteins by Flow-Though Radio-HPLC

As an alternative to enrichment by gel electrophoresis, a protocol is developed to identify and isolate the radiolabeled synthases using a flow-through radioisotope detector attached to a HPLC system. Proteins in samples of crude lysates are exposed to tritiated inhibitor and subsequently separated using a reverse-phase C4 column and eluted using a 40-90% acetonitrile gradient over 45 minutes. Eluting radiolabeled fractions are identified using a radiolabel-detector. Corresponding fractions from non-radiolabeled CP-GGPP exposed lysates are isolated and proteolytically digested. The resulting peptide fragments are combined, separated by LC, and sequenced on a high-resolution tandem MS.

Tandem-MS Sequencing of Tagged Synthase Peptide

Tagged peptides derived from terpene synthases after trypsin proteolysis are identified by detecting the presence of the tag itself. Samples are modified with the inhibitor and samples from the enzymatic reaction are taken at intervals (15 min, 30 min, 1 h, 2 h, 4 h, and 12 h) and subsequently trypsin digested. Reverse-phase liquid chromatography is used to separate peptides on a C18 micro-column (300 μm ID, 15 cm length). Ten pmoles of the proteolytic digest is loaded onto the column and eluted with a 2 to 50% acetonitrile gradient over 50 minutes.

Each peptide is fully sequenced using tandem MS. Tagged peptides are identified through the detection of sequences with "unnatural" amino acids corresponding to residues modified by the presence of the CP-GGPP tag moiety (271.2 amu). Non-natural amino acids are identified by the software in a process very similar to the identification of alkylated cysteine residues, a common practice in the analysis of tryptic peptides in proteomics. Similar techniques have been used to identify the catalytic residues for other mechanism-based inhibitors (Garcia-Alles et al. (2002) *J Biol Chem* 277(9): 6934-42; Yang et al. (2000) *J Biol Chem* 275(35):26674-82).

Example 3

Isolation of Full Length Diterpene Synthase Gene Sequence(s)

Full length diterpene synthases genes are isolated by PCR of adaptor-ligated cDNA or from a partial genomic library. PCR amplification of adaptor-ligated cDNA uses one gene specific primer and one primer which anneals to the double stranded adaptor ligated to the cDNA (Chenchik et al. (1996) *Biotechniques* 21(3):526-34). For purposes of this experiment, synthase specific, degenerate primers are designed to hybridize to all possible codon sets corresponding to the specific peptide sequences identified from the diterpene synthase inhibitor tagging LC-tandem-MS experiments previously described. cDNA is synthesized according to well established protocols using both random hexamer primers (for archeal and bacterial mRNA) and an oligo-dT approach (for eukaryotic mRNA) in order to assure coverage of mRNA from *Erythropodium* and its symbionts. The Marathon cDNA amplification kit from BD Biosciences Clontech (Palo Alto, Calif.) is employed to amplify and clone the full length cDNAs. In order to amplify both the 5' and 3' ends of the cDNA, synthase specific degenerate oligonucleotide primers, which anneal to both the top and bottom strands, are used in conjunction with adaptor specific primers. In instances where only one end of the cDNA is successfully amplified, it is sequenced to allow for the design of an alternate primer (non-degenerate). Full length cDNAs are amplified and cloned directly from adaptor-ligated cDNA using flanking 5' and 3'-synthase-specific primers established from the DNA sequences of the 5' and 3'-ends. Alternatively, the amplified 5' and 3' ends are gel purified and spliced together by PCR using the overlap extensions created by the use complementary gene specific PCR primers.

As an alternative to isolating synthase genes by PCR directly from mRNA, synthase genes are obtained from a partial genomic library. This approach has the advantage of potentially isolating gene clusters encoding several enzymes of the eleutherobin biosynthetic pathway if the eleutherobin isolated from *E. caribaeorum* is synthesized by a prokaryotic symbiont. Actinomycetes have recently been identified as common symbionts of marine organisms (Zheng et al. (2000) *FEMS Microbiol Lett* 188(1):87-91; Webster et al. (2001) *Appl Environ Microbiol* 67(1):434-44). Since Actinomycetes are known to harbor genes clusters encoding the synthesis of complex secondary metabolites including diterpenes (Dairi et al. (2001) *J Bacteriol* 183(20):6085-94), an eleutherobin biosynthetic gene cluster may be found to include all the genes necessary to modify the olefin backbone. Since hybridization with degenerate oligonucleotides presents problems with respect to specificity and sensitivity, gene probes to be used for Southern blot analysis are generated by PCR. PCR is performed using degenerate primer pairs (forward and reverse) designed from diterpene synthase specific peptide sequences identified by MS. Sets of four pairs of primers are used in each PCR reaction, which will allow for the sampling of all possible primer pairs in fewer PCR reactions. Genomic DNA are digested with several endonucleases, Southern blotted and probed with radiolabeled nucleic acid. To generate partial libraries containing the diterpene synthase gene(s), DNA bands that hybridize to the probe(s) are excised from the gel and ligated into a pBluescript plasmid. Individual clones from the library are screened by PCR with the identical set of primers used to generate the probe.

Example 4

Expression of Diterpene Synthases in *E. coli* and Determination of Synthase Product Identified diterpene synthases are cloned into pTRC99A (Pharmacia) and expressed in an *E. coli* host expressing the full mevalonate pathway and GGPP synthase (Wang et al. (1999) *Biotechnol* Bioeng 62(2:235-41). Terpene backbones produced by the cells are extracted using ethyl acetate, and purified using TLC. Products are confirmed as diterpene synthases using MS, and analyzed by NMR in order to determine the structure of each compound produced.

Overnight cultures of *E. coli* DH10B pMEVT pMBIS with GGPP synthase and a putative diterpene synthase are inoculated with stationary phase inocula, grown for two hours, followed by the expression of the mevalonate pathway and the putative diterpene synthase with 0.5 mM IPTG. Cells are grown until stationary phase. One ml samples are centrifuged, and the pellet is suspended in 1 ml of phosphate buffered saline. Diterpenes are extracted from the sample with an equal volume of ethyl acetate and subsequently purified by silica TLC (with hexane/diethyl ether 97:3 v/v). Diterpenes are located on the plate with UV light excitation of imbedded fluorescein. Diterpene spots are scraped from the plate, eluted with hexane, and analyzed by GC-MS and NMR.

It may be the case that the gene does not express well in *E. coli* due to differences in codon preference. To address this problem, genes of poorly producing putative diterpene synthases are synthesized de novo with *E. coli* codon preferences. After the gene sequence is codon optimized for expression in *E. coli* using standard software (for example, Calcgene or DNA Works), 40-basepair oligonucleotides are used for each strand of the full-length gene. The 40-bp oligonucleotides overlap by 20-bp with the oligonucleotides in the bottom strand. All of the oligonucleotides for the two strands are mixed in a single tube and assembled in a PCR thermocycler. The full-length gene is recovered from a mixture of full-length and partial products using the outer-most primers, cloned into an expression vector, transformed into the GGPP-overproducing *E. coli* strain, and screened for function by analyzing the terpene product using GC-MS analysis.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of identifying a terpene synthase in a biological sample comprising an enzyme, the method comprising:
    (a) contacting the sample with a suicide substrate that covalently modifies a terpene synthase, wherein said contacting results in covalent binding of the substrate to an amino acid of the enzyme to form a covalently modified enzyme; and (b) determining an amino acid sequence of at least a portion of the covalently modified enzyme, thereby identifying the enzyme as a terpene synthase.

2. The method of claim 1, wherein the sample is a biological sample.

3. The method of claim 1, wherein the covalently modified enzyme is isolated before said determining step.

4. The method of claim 3, wherein said suicide substrate is radiolabeled.

5. The method of claim 3, wherein the covalently modified enzyme is isolated by one-dimensional isoelectric focusing.

6. The method of claim 3, wherein the covalently modified enzyme is isolated by two-dimensional gel electrophoresis.

7. The method of claim 3, wherein the covalently modified enzyme is isolated by fast protein liquid chromatography.

8. The method of claim 3, wherein the covalently modified enzyme is isolated by size-exclusion chromatography.

9. The method of claim 1, wherein the covalently modified enzyme is proteolytically cleaved with a first proteolytic enzyme before amino acid sequencing.

10. The method of claim 9, wherein the covalently modified enzyme is proteolytically cleaved with a second proteolytic enzyme before amino acid sequencing.

11. The method of claim 1, wherein said suicide substrate is a cyclopropyl-modified polyprenyl diphosphate.

12. The method of claim 11, wherein said cyclopropyl-modified polyprenyl diphosphate is selected from the group consisting of cyclopropylidene farnesyl diphosphate, cyclopropylidene geranyl diphosphate, cyclopropylidene geranylgeranyl diphosphate, cyclopropylidene geranylfarnesyl diphosphate, cyclopropylidene hexaprenyl diphosphate, cyclopropylidene heptaprenyl diphosphate, cyclopropylidene octaprenyl diphosphate, cyclopropylidene solanesyl diphosphate, cyclopropylidene decaprenyl diphosphate, cyclopropylidene undecaprenyl diphosphate, and cyclopropylidene dehydrodolichyl diphosphate.

13. The method of claim 1, wherein said suicide substrate is a vinyl analog of a polyprenyl diphosphate.

14. The method of claim 13, wherein the vinyl analog is selected from the group consisting of 6-methylidene farnesyl diphosphate, 11-methylidene geranyl diphosphate, 16-methylidene geranylgeranyl diphosphate, 21-methylidene geranylfarnesyl diphosphate, 26-methylidene hexaprenyl diphosphate, 31-methylidene heptaprenyl diphosphate, 36-methylidene octaprenyl diphosphate, 41-methylidene solanesyl diphosphate, 46-methylidene decaprenyl diphosphate, and 51-methylidene undecaprenyl diphosphate.

15. The method of claim 1, wherein said amino acid sequence determination is by tandem mass spectrometry analysis.

16. The method of claim 1, wherein said amino acid sequence determination is by Edman degradation.

17. The method of claim 1, further comprising generating a nucleic acid having a degenerate nucleotide sequence encoding the amino acid sequence, wherein the nucleotide sequence is based on the amino acid sequence determined in step (b).

18. The method of claim 17, wherein the nucleic acid is suitable for use as a hybridization probe to detect a nucleic acid that comprises a nucleotide sequence that encodes the enzyme.

19. The method of claim 17, wherein the nucleic acid is suitable for use to initiate synthesis of a nucleic acid amplification product by a DNA polymerase.

* * * * *

UNITED STATES PATENT AND TRADEMARK OFFICE
CERTIFICATE OF CORRECTION

PATENT NO. : 7,745,108 B2  
APPLICATION NO. : 10/581975  
DATED : June 29, 2010  
INVENTOR(S) : Newman et al.

Page 1 of 1

It is certified that error appears in the above-identified patent and that said Letters Patent is hereby corrected as shown below:

In the specification:

The following text should be added between the "CROSS-REFERENCE" and "FIELD OF THE INVENTION" paragraphs of column 1:

--STATEMENT REGARDING FEDERALLY SPONSORED RESEARCH

This invention was made with Government support under 2001-52104-11228 awarded by the U.S. Department of Agriculture. The Government has certain rights in the invention.--

Signed and Sealed this
Thirty-first Day of May, 2016

Michelle K. Lee
*Director of the United States Patent and Trademark Office*